United States Patent
Chiao et al.

(10) Patent No.: US 9,163,313 B2
(45) Date of Patent: Oct. 20, 2015

(54) AMORPHOUS IRO$_X$ FILM PH SENSOR

(71) Applicant: Board of Regents, The University of Texas System, Austin, TX (US)

(72) Inventors: Jung-Chi Chiao, Grand Prairie, TX (US); Wen-Ding Huang, Arlington, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 126 days.

(21) Appl. No.: 14/037,848

(22) Filed: Sep. 26, 2013

(65) Prior Publication Data

US 2014/0027295 A1    Jan. 30, 2014

Related U.S. Application Data

(60) Division of application No. 12/911,329, filed on Oct. 25, 2010, now Pat. No. 8,552,730, which is a continuation-in-part of application No. 12/867,526, filed as application No. PCT/US2009/034161 on Feb. 13, 2009, now abandoned.

(60) Provisional application No. 61/028,343, filed on Feb. 13, 2008.

(51) Int. Cl.
  *H01L 21/20*   (2006.01)
  *C23C 28/00*   (2006.01)
  *G01N 27/403*  (2006.01)
  *G01N 27/416*  (2006.01)

(52) U.S. Cl.
  CPC ............ *C23C 28/345* (2013.01); *G01N 27/403* (2013.01); *G01N 27/4167* (2013.01)

(58) Field of Classification Search
  None
  See application file for complete search history.

(56) References Cited

U.S. PATENT DOCUMENTS 8,552,730 B2 *  10/2013  Chiao et al. .................... 324/438

OTHER PUBLICATIONS

Sheppard, Jr. et al. "pH Measurement", CRC Press LLC (1999).
Kim et al. "A Novel pH Microsensor with a Built-in Reference Electrode", J Korean Physical Society, 43(5):769-772 (2003).
Liu et al. "Ion-sensitive field-effect transistor based pH sensors using nano self-assembled polyelectrolyte/nanoparticie multilayer films", Sensors and Actuators B, 123;148-152 (2007).
Han et al. "A gastroesophageal tract pH sensor based on the H+-ISFET and the monitoring system for 24 h", Sensors and Actuators B, 68:203-209 (2000).
Pasztor et al, "Iridium oxide-based microelectrochemical transistors for pH sensing", Sensors and Actuators B, 12:225-230 (1993).

(Continued)

*Primary Examiner* — Seahvosh Nikmanesh
(74) *Attorney, Agent, or Firm* — Parks Wood LLC; Stephen J. Terrell

(57) ABSTRACT

The present invention provides a pH sensing apparatus that includes a flexible polymer substrate, one or more amorphous iridium oxide film sensor electrodes disposed on the flexible polymer substrate, and a reference electrode corresponding to each amorphous iridium oxide film sensor electrode. Each reference electrode is disposed on the flexible polymer substrate in close proximity to the corresponding amorphous iridium oxide film sensor electrode. The amorphous iridium oxide film sensor electrodes provide a potential in reference to the reference electrodes that varies according to a pH of a substance contacting the amorphous iridium oxide film sensor electrodes and the reference electrodes.

7 Claims, 24 Drawing Sheets

(56) References Cited

OTHER PUBLICATIONS

Wolfbeis, Otto S. "Fiber-Optic Chemical Sensors and Biosensors", Anal Chem, 76:3269-3289 (2404).
Grant et al. "A sol-gel based fiber optic sensor for local blood pH measurements", Sensors and Actuators B, 45:35-42 (1997).
Dong et al. "Broad range pH sensor based on sol-gel entrapped indicators on fibre optic", Sensors and Actuators B, 129:94-98 (2008).
Jin et al. "An Improved optical pH sensor based on polyaniline", Sensors and Actuators B, 71:118-122 (2000).
Safavi et al. "Novel optical pH sensor for high and low pH values", Sensors and Actuators B, 90:143-150 (2003).
Alvarado-Mendez et al., "Design and characterization of pH sensor based on sol-gel silica layer on plastic optical fiber", Sensors and Actuators B, 106:518-522 (2005).
Sheppard, Jr. et al. "Microfabricated conductimetric pH sensor", Sensors and Actuators B, 28:95-102 (1995).
Gerlach et al. "Chemical pH sensors based on the swelling behavior of hydrogels", Sensors and Actuators B, 111-112:555-561 (2005).
Bashir et al. "Micromechanical cantilever as an ultrasenstive pH microsenser", Applied Physics Letters, 81 (16):3091-3093 (2002).
Fog et al. "Electronic Semiconducting Oxides as pH Sensors", Sensors and Actuators, 5:137-146 (1984).
Mikolajick et al. "The pH-sensor properties of tantaium pentoxide films fabricated by metal organic low pressure chemical vapor deposition", Sensors and Actuators B, 44:262-267 (1997).
Kinlen et al. "A solid-state pH sensor based on a Nafion-coated Iridium oxide Indicator electrode and a polymer-based silver chloride reference electrode", Sensors and Actuators B, 22:13-25 (1994).
McMurray et al. "Novel thick-film pH sensors based on ruthenium dioxide-glass composites", Sensors and Actuators B, 28:9-15 (1995).
Olthius, Wouter "Chemical and physical FET-based sensors or variations on an equation", Sensors and Actuators B, 105:96-103 (2005).
Liao et al. "Preparation and characteristics of ruthenium dioxide for pH array sensors with real-time measurement system", Sensors and Actuators B, 128:603-612 (2008).
Tsai et al. "Study on the sensing characteristics and hysteresis effect of the tin oxide pH electrode", Sensors and Actuators B, 108:877-882 (2005).
Yao et al. "A pH Electrode Based on Melt-Oxidized Iridium Oxide", J Electrochemical Society, 148(4)H29-H36 (2001).
Dobson et al. "EMF Measurements of Cells Employing Metal-Metal Oxide Electrodes in Aqueous Chloride and Sulphate Electrolytes at Temperatures Between 25-250C", Electrochimica Acta, 21:527-533 (1976).
Katsube et al. "pH Sensitive Sputtered Iridium Oxide Films", Sensors and Actuators, 2 :399-410 (1982).
Lauks et al. "pH Dependent Voltammetry of Iridium Oxide Films", Solid Slate Ionics, 11:19-29 (1983).
Yamanaka, Kazusuke "Anodically Electrodeposited Iridium Oxide Films (AEIROF) from Alkaline Solutions for Electrochromic Display Devices", Japanese J Applied Physics, 28(4):632-637 (1989).
Petit et al. "Anodic electrodeposition of Iridium oxide films", J Electroanalytical Chemistry, 444:247-252 (1998).
Marzouk et al. "Electrodeposited Iridium Oxide pH Electrode for Measurement of Extracellular Myocardial Acidosis during Acute Ischemia", Anal Chem, 70:5054-5061(1998).
Ges et al. "Thin-Film IrOx pH microelectrode for microfluidic-based microsystems", Biosensors and Bioelectronics, 21:248-256 (2005).
Nishio et al. "Preparation and properties of electrochromic Iridium oxide thin film by sol-gel process", Thin Solid Films, 350:96-100 (1999).
Osaka et al. "Iridium oxide films via sol-gel processing", J Non-Crystalline Solids, 178:313-319 (1994).
Nishio et al. "Electrochromic thin films prepared by sol-gel process", Solar Energy Materials & Solar Cells, 68:279-293 (2001).

Brinker et al. "Sol-Gel Science: The Physics and Chemistry of Sol-Gel Processing", Academic Press, pp. 788-798 (1990).
Grant et al. "In vitro and in vivo measurements of fiber optic and electrochemical sensors to monitor brain tissue pH", Sensors and Actuators B, 72:174-179 (2001).
O'Hare et al. "Metal-metal oxide pH sensors for physiological application", Medical Engineering & Physics, 28:982-988 (2006).
Clark et al. "Modeling the Response Time of an In Vivo Glucose Affinity Sensor", Biotechnol Prog, 15:259-266 (1999).
Visch et al. "pH Measurements with an Ion Sensitive Field Effect Transistor in the Mouth of Patients with Xerostomia", IEEE Trans on Biomedical Engineering, 38(4)353-356 (1991).
Gillies et al. "pH Imaging—A Review of pH Measurement Methods and Applications in Cancers", IEEE Engineering in Medicine and Biology, pp. 58-64 (2004.).
Auerbach et al. "Hypothermia Effects Microsensor Measurement of Tissue pH", IEEE, ppb830-831 (1994).
Kress-Rogers, Erika "Solid-state pH sensors for food applications", Trends in Food Science and Tech, 2:320-324 (1990).
Bohnke et al. "pH sensors with lithium lanthanum titanate sensitive material: applications in food industry", Sensors and Actuators B, 89:240-247 (2003).
Smiechowski et al. "Iridium oxide sensors for acidity and basicity detection in industrial lubricants", Sensors and Actuators B, 96:261-267 (2003).
Pungor, Erno "The Theory of Ion-Selective Electrodes", Japan Society of Analytical Chemistry, 14:249-256 (1998).
Cranny et al. "Thick film silver-silver chloride reference electrodes" Meas Sci Technol, 9:1557-1565 (1998).
Van Muylder et al. "Iridium", Nati Associ of Corrosion Engineers, pp. 374-377 (1974).
Ardizzone et al. "Properties of Thermally Prepared Iridium Dioxide Electrodes", J Electroanal Chem, 126:287-292 (1981).
Hendrikse et al. "A method of reducing oxygen induced drift in iridium oxide pH sensors", Sensors and Actuators B, 53:97-103 (1998).
Olthuis et al. "pH Sensor Properties of Electrochemically Grown Iridium Oxide", Sensors and Actuators B, 2:247-266 (1990).
Andreas et al. "Hydrous Ir Oxide Film Properties at Sol-Gel Derived Ir Nanoparticles", J Electorchemical Society, 147:4598-4604 (2000).
Yue et al. "A novel paper pH sensor based on polypyrrole", Sensors and Actuators B, 32:33-39 (1996).
Ativanichayaphong et al. "An Implantable, Wireless and Batteryless Impedance Sensor Capsule for Detecting Acidic and Non-Acidic Reflux", Oral Presentation, Digestive Disease Week, San Diego, CA (May 2008).
Schneider et al. "Influence of pH on wound-healing: a new perspective for wound therapy?", Arch Dermatol Res, 298:413-420 (2007).
Harrison et al. "Micro-Electrode Measurement of Skin pH in Humans During Ischaemia, Hypoxia and Local Hypothermia", J Physiol, 291:339-350 (1979).
Shorrock et al. "The Exploration of Tissue pH in Wounds and its Relationship to Bacterial Contamination", Worcester Polytechnic Institute, pp. 20-24 (2000).
Jansson et al. "pH effects on experimental wound healing of human fibroblasts in vitro", Eur J Oral Sciences, 103:148-155 (1995).
Bordi et al. "Use of an Iridium Electrode for Direct Measurement of pI of Proteins After Isoelectric Focusing in Polyacrylamide Gel", Biochimica el Biophysica Acta, 453:192-199 (1976).
Da Slilva et al. "Development of low-cost metal oxide pH electrodes based on the polymeric precursor method", Analytica Chimica Acta, 616:36-41 (2008).
Chen et al. "Optimization of Inductive RFID Technology", IEEE Intl Symposium on Electronics and the Environment, pp. 82-87 (2001).
Haile et al. "Oscillator Circuits for RTD Temperature Sensors", Microchip Technology Inc., AN895 (2004).

* cited by examiner

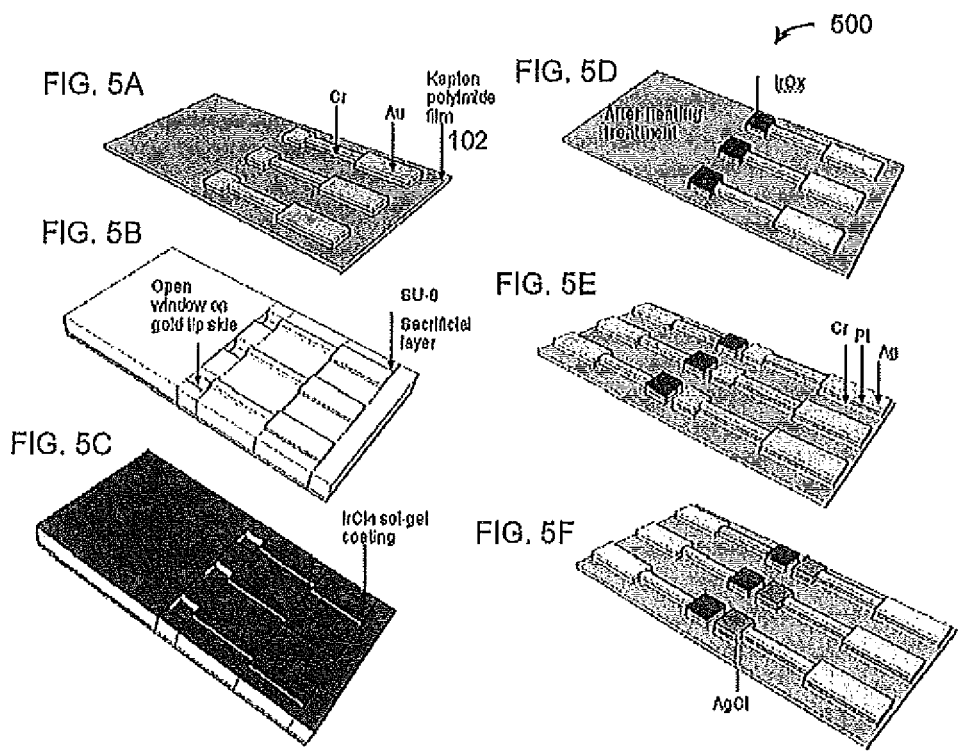
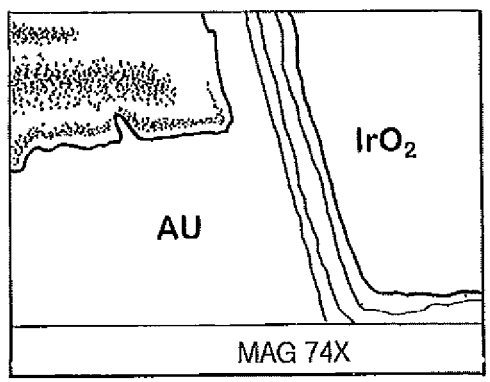
FIGURE 6A
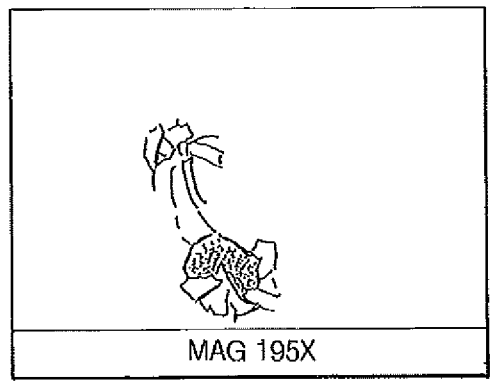
FIGURE 6B

Figure 11 Temporal response in titration (a) from pH=3.9 to pH=11, (b) from pH=12 to pH=3.5, and (c) from the dry condition to a solution droplet with pH=4.01.

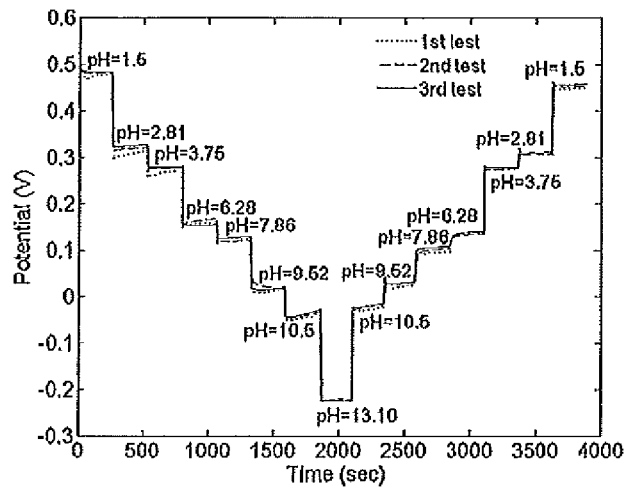
Figure 12 Measured results for reversibility and repeatability experiments with pH varying from 1.5 to 13.1, and back to 1.5 in titration. The experiments were repeated by three cycles.
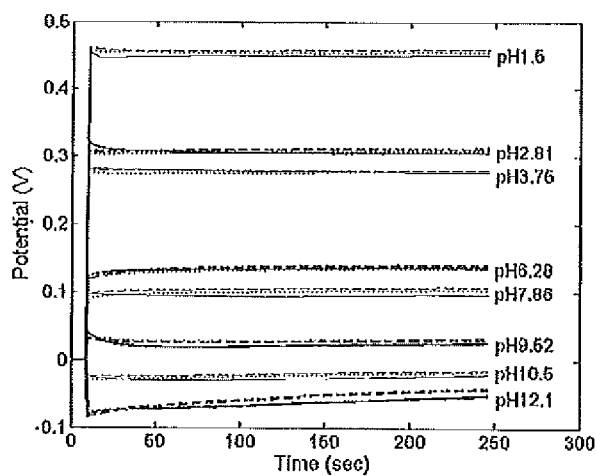
Figure 13 Measured potentials in eight different pH levels to demonstrate stability and repeatability.

Figure 19 Block diagrams of the passive wireless pH sensor system.

Figure 20 The relaxation oscillator design in the transponder.

Figure 21 Measured sensitivity of our wireless pH sensor system in terms of frequency and potential.

Figure 22 Stability test for our wireless pH sensor system.

Figure 23 Responses in the titration test for the wireless pH sensor system.

Figure 30 Measured potential with the flexible pH sensors in fish filets stored at 25° and 5°C.

Figure 31 The modulated frequencies transduced from the fish filets with the wireless pH sensor tag wrapped in the package.

AMORPHOUS IRO$_X$ FILM PH SENSOR

CROSS REFERENCE TO RELATED APPLICATIONS

This application is a divisional of U.S. application Ser. No. 12/911,329, filed Oct. 25, 2010, now issued as U.S. Pat. No. 8,552,730, which is a continuation-in-part of U.S. application Ser. No. 12/867,526, now abandoned, which is a national phase of International Application No. PCTIUS20091034161 filed Feb. 13, 2009, which claims benefit of Provisional Application No. 61/028,343, filed Feb. 13, 2008, the content of which is expressly incorporated herein by reference.

FIELD OF INVENTION

The present invention relates in general to the field of sensors, and more particularly to an amorphous iridium oxide film pH sensor.

BACKGROUND ART pH sensors are used in clinics, laboratories and industrial factories since many biological and chemical reaction mechanisms are pH dependent. Conventional glass-type electrodes have been widely used; however, they still have certain disadvantages in specific applications. The glass rod sensor configuration is difficult to use for in vivo biomedical, clinical or food monitoring applications due to the brittleness of glass, size limitations and the lack of deformability. To achieve small sizes and robust design, ion-sensitive field-effect transistor (iSFET) pH sensors [1-5], optical fiber pH sensors [1, 6-11], hydrogel film pH sensors [12-14], and solid sate pH sensors [1, 15-18] have been proposed. iSFET sensors have power consumption concerns due to the field-effect transistor (FET) operational requirements [19]. Hydrogel film pH sensors utilize the physical properties of the pH-response swelling and shrinking polymer to measure resistance changes [12]. The sensor structure design and polymer layer fabrication process can be complicated and expensive [13]. Optical pH sensors also have power consumption issues due to the use of light sources. The system including optical devices could be expensive and unsuitable for implantation [1, 7-8, 10-11].

Various solid-state metal oxides have been investigated for pH sensing electrodes [1, 15] including $PtO_2$, $IrO_x$, $RuO_2$, $OsO_2$, $Ta_2O_5$, $RhO_2$, $TiO_2$ and $SnO_2$ as the pH sensing films. The pH sensitivity, selectivity, working range, and hysteresis indicate sensing performance. $IrO_x$, $RuO_2$ and $SnO_2$ have been demonstrated with more advantages in sensor performance for various applications [22]. $RuO_2$ [18, 20] and $SnO_2$ [21] show near Nernstian responses in wide pH ranges. However, $SnO_2$ and $RuO_2$ presented hysteresis and drift problems leading to potential calibration issues and unstable responses [20, 21]. Iridium oxide film (IROF) has performed outstanding stability over wide pH rages, rapid responses, less hysteresis and high durability, which have also been demonstrated at high temperature up to 250° C. [23].

There are different fabrication methods for IROF including sputtering deposition [23, 24], electrochemical deposition [25-29], thermal oxidation [23], and sol-gel [30-32] processes. The sputtering iridium oxide film (SIROF) deposition process is costly due to the target cost. The oxygen and argon pressure ratios, position of the target, deposition rate, and RF powers during the fabrication processes all affect the pH sensing parameters such as potential drifts and redox interference [22]. Anodic electrochemical deposition presents an economical way for iridium oxide thin film fabrication. The anodic iridium oxide thin film (AIROF) process is based on electrolysis of a solution containing iridium complexes. The iridium tetrachloride compound has been widely used as a deposition agent [26-29] such as the commonly used Yamanaka solution [26]. The pH value of the deposition solution, solution temperature and current density control affect the deposition efficiency [26-29]. A precise power supply system as potentiostate is required in the electro-deposition process for thickness and film quality control. For thermal oxidation process, it requires a high temperature ranging from 500 to 800° C. [17, 22]. The film made by thermal oxidation can be thicker than the AIROF with more stable potentials [22, 23]. However, the film surface has a tendency to crack after the high temperature treatment. The adhesion property of the cracked film then becomes an issue. The high temperature treatment also becomes a limitation during sensor fabrication, especially for the use of polymer and photoresist, which often can not survive at a temperature above 200° C. The sol-gel IROF deposition process has been demonstrated [32] with dip coating [32, 33] and heat treatment [31, 32] procedures. Sol-gel deposition provides a simpler and economical fabrication approach.

There is, therefore, a need for a cost efficient, simpler fabrication and lower power consumption, a metal-oxide pH sensor with deformability on a flexible substrate.

SUMMARY OF THE INVENTION

The present invention provides a sol-gel process to make IROF pH sensor arrays on flexible polyimide substrates. An amorphous and uniform IROF was formed with 300° C. thermal oxidation, Our IROF pH sensor provided good stability with less drifts, high selectivity, fast response, reversibility with low power consumption advantages along with the simpler and potentially lower cost fabrication processes. With these features, our sensors could be used for in vivo biomedical [34, 35], biological [36, 37], clinical [38-40], food monitoring [41, 42] and lubricant applications [43].

Both iridium oxide sensing films and Ag/AgCl reference electrodes were formed on a polyimide flexible substrate by sol-gel, dip-coating and thermal oxidation processes. Fabrication, characterization, and dynamic test results of a deformable potentiometric pH electrode were presented. The $IrO_x$ pH sensors exhibited promising sensing performance with a super-Nernstian response of sensitivity between 69.6 and 71.6 mV/pH in the pH range from 1.9 to 12 at 25° C. A response time was obtained at less than 7 seconds. The pH electrodes showed high selectivity and reversibility in different acid and alkaline solutions. The deformable pH electrodes provide the advantage of accommodating sensors in small spaces or conform to curved surfaces. Our deformable pH sensor array responded with distinct potentials to various pH values at different positions inside a 1.5-cm diameter tube.

The present invention provides a pH sensing apparatus that includes a flexible polymer substrate, one or more amorphous iridium oxide film sensor electrodes disposed on the flexible polymer substrate, and a reference electrode corresponding to each amorphous iridium oxide film sensor electrode. Each reference electrode is disposed on the flexible polymer substrate in close proximity to the corresponding amorphous iridium oxide film sensor electrode. A first electrical contact pad corresponding to each amorphous iridium oxide film sensor electrode is disposed on the flexible polymer substrate and electrically connected to the corresponding amorphous iridium oxide sensor. A second electrical contact pad corresponding to each reference electrode is disposed on the flexible polymer substrate and electrically connected to the corresponding reference electrode. The amorphous iridium oxide film sensor electrodes provide a potential in reference to the reference electrodes that varies according to a pH of a substance contacting the amorphous iridium oxide film sensor electrodes and the reference electrodes.

In addition, the present invention provides a method for fabrication one or more pH sensors by depositing a chromium layer and a gold layer on a flexible polymer substrate to define a sensor electrode and a first electrical contact pad, depositing a sacrificial layer on the first electrical contact pad and the flexible polymer substrate, coating the sacrificial layer and the sensor electrode with an iridium oxide thin film, heating the sensor electrode to form an amorphous iridium oxide sensor electrode, removing the sacrificial layer, depositing a chromium layer, a platinum layer and a silver layer on the flexible polymer substrate to define a reference electrode and a second electrical pad, and electroplating the silver layer.

The present invention also provides a device for detecting spoilage in a food that includes a biocompatible pH sensing apparatus for physical contact with the food. The pH sensing apparatus includes a flexible polymer substrate, one or more amorphous iridium oxide film sensor electrodes disposed on the flexible polymer substrate, and a reference electrode corresponding to each amorphous iridium oxide film sensor electrode. Each reference electrode is disposed on the flexible polymer substrate in close proximity to the corresponding amorphous iridium oxide film sensor electrode. A first electrical contact pad corresponding to each amorphous iridium oxide film sensor electrode is disposed on the flexible polymer substrate and electrically connected to the corresponding amorphous iridium oxide sensor. A second electrical contact pad corresponding to each reference electrode is disposed on the flexible polymer substrate and electrically connected to the corresponding reference electrode. The amorphous iridium oxide film sensor electrodes provide a potential in reference to the reference electrodes that varies according to a pH of the food contacting the amorphous iridium oxide film sensor electrodes and the reference electrodes. A passive radio frequency identification chip is electrically connected to the first and second electrical contact pads. A tag antenna electrically connected to the passive radio frequency identification chip. The present invention also provides a system for detecting spoilage in a food by adding a radio frequency identification reader comprising a computer connected to an antenna. The present invention also a provides a system wirelessly detecting the spoilage of food by using a flexible pH sensing tag in the food packaging along with a passive RE telemetry circuit embedded in the food product label as freshness indicator which allows a wireless reader to interrogate the pH level in the food remotely. The present invention also provides a system for wirelessly detecting the spoilage of food using a wireless sensor tag that includes a pH sensing apparatus comprising a flexible polymer substrate, one or more amorphous iridium oxide film sensor electrodes disposed on the flexible polymer substrate, and a reference electrode corresponding to each amorphous iridium oxide film sensor electrode. Each reference electrode is disposed on the flexible polymer substrate in close proximity to the corresponding amorphous iridium oxide film sensor electrode. A first electrical contact pad corresponding to each amorphous iridium oxide film sensor electrode is disposed on the flexible polymer substrate and electrically connected to the corresponding amorphous iridium oxide sensor. A second electrical contact pad corresponding to each reference electrode is disposed on the flexible polymer substrate and electrically connected to the corresponding reference electrode. The amorphous iridium oxide film sensor electrodes provide a potential in reference to the reference electrodes that varies according to a pH of the food contacting the amorphous iridium oxide film sensor electrodes and the reference electrodes.

Moreover, the present invention provides a bandage for detecting a condition of a wound that includes a wound dressing material and a biocompatible pH sensing apparatus attached to the wound dressing material for physical contact with the wound. The pH sensing apparatus includes a flexible polymer substrate, one or more amorphous iridium oxide film sensor electrodes disposed on the flexible polymer substrate, and a reference electrode corresponding to each amorphous iridium oxide film sensor electrode. Each reference electrode is disposed on the flexible polymer substrate in close proximity to the corresponding amorphous iridium oxide film sensor electrode. A first electrical contact pad corresponding to each amorphous iridium oxide film sensor electrode is disposed on the flexible polymer substrate and electrically connected to the corresponding amorphous iridium oxide sensor. A second electrical contact pad corresponding to each reference electrode is disposed on the flexible polymer substrate and electrically connected to the corresponding reference electrode. The amorphous iridium oxide film sensor electrodes provide a potential in reference to the reference electrodes that varies according to a pH of the wound contacting the amorphous iridium oxide film sensor electrodes and the reference electrodes. A passive radio frequency identification chip is electrically connected to the first and second electrical contact pads. A tag antenna electrically connected to the passive radio frequency identification chip. The present invention also provides a system for detecting the condition of a wound by adding a radio frequency identification reader comprising a computer connected to an antenna.

BRIEF DESCRIPTION OF THE DRAWINGS

Further benefits and advantages of the present invention will become more apparent from the following description of various embodiments that are given by way of example with reference to the accompanying drawings:

FIGS. 5A-5F illustrate a method for fabricating a pH sensor in accordance with another embodiment of the present invention;

FIGS. 6A-6B are photos of the $IrO_x$ films treated at 300° C. (amorphous) and 550° C. (crystalline), respectively, in accordance with another embodiment of the present invention;

FIG. 12 is a graph showing results for reversibility and repeatability experiments in accordance with another embodiment of the present invention;

FIG. 13 is a graph showing results for stability and repeatability tests in accordance with another embodiment of the present invention;

DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Figure 1:
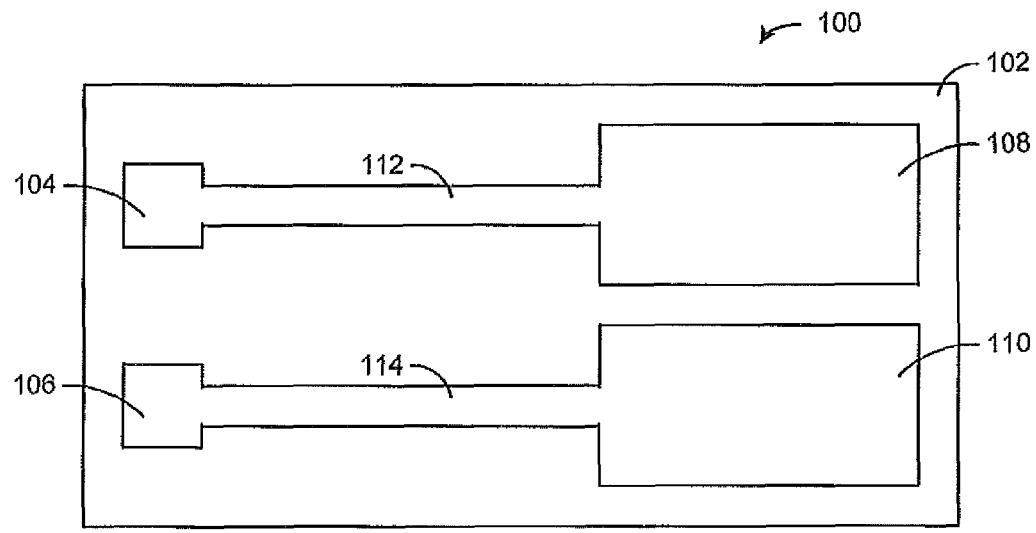
FIG. 1 illustrates a pH sensor in accordance with one embodiment of the present invention.

Now referring to FIG. 1, a pH sensor 100 in accordance with one embodiment of the present invention is shown. The pH sensing apparatus 100 includes a flexible polymer substrate 102, an amorphous iridium oxide film sensor electrode 104 disposed on the flexible polymer substrate 102 and a reference electrode 106 disposed on the flexible polymer substrate 102 in close proximity to the amorphous iridium oxide film sensor electrode 104. In addition, a first electrical contact pad 108 disposed on the flexible polymer substrate 102 and is electrically connected to the amorphous iridium oxide sensor 104 via a conductive trace, connector or pathway 112. Similarly, a second electrical contact pad 110 is disposed on the flexible polymer substrate 102 and electrically connected to the reference electrode via a conductive trace, connector or pathway 114. As will be described in more detail below, the amorphous iridium oxide film sensor electrode 104 provides a potential in reference to the reference electrode 106 that varies according to a pH of a substance contacting the amorphous iridium oxide film sensor electrode 104 and the reference electrode 106. Note that the present invention is not limited to the specific orientation shown in FIG. 1. Moreover, FIG. 1 is not to scale. As a result, any suitable orientation of the components can be used, and the components can be of any suitable geometric shape. One example of a process for fabricating the pH sensor 100 will be described in more detail below.

Figure 2:
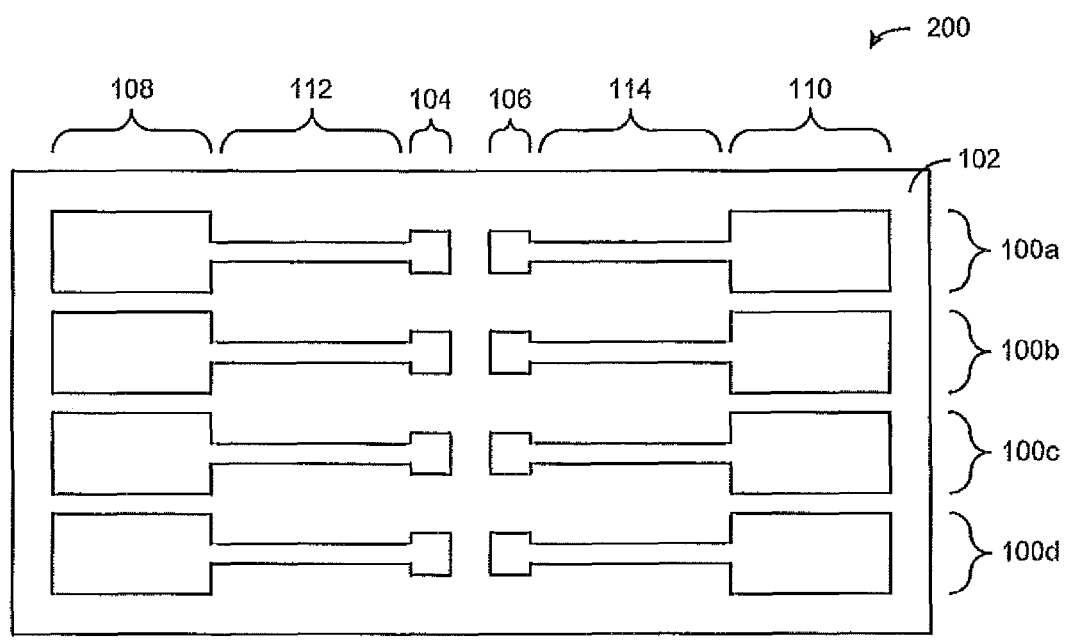
FIG. 2 illustrates an array of pH sensors in accordance with another embodiment of the present invention.

Referring now to FIG. 2, an array 200 of pH sensors in accordance with another embodiment of the present invention is shown. As shown, the pH sensor array 200 includes four pH sensors 100a, 100b, 100c and 100d disposed on a flexible polymer substrate 102. The array can contain any number of pH sensors 100. The four amorphous iridium oxide film sensor electrodes 104 are disposed on the flexible polymer substrate 102. A reference electrode 106 corresponding to each amorphous iridium oxide film sensor electrode 104 is disposed on the flexible polymer substrate 102 in close proximity to the corresponding amorphous iridium oxide film sensor electrode 104. A first electrical contact pad 108 corresponding to each amorphous iridium oxide film sensor electrode 104 is disposed on. the flexible polymer substrate 102 and electrically connected to the corresponding amorphous iridium oxide sensor 104 via a conductive trace, connector or pathway 112. A second electrical contact pad 110 corresponding to each reference electrode 106 is disposed on the flexible polymer substrate 102 and electrically connected to the corresponding reference electrode 105 via a conductive trace, connector or pathway 114. The amorphous iridium oxide film sensor electrodes 104 provide a potential in reference to the reference electrodes 104 that varies according to a pH of a substance contacting the amorphous iridium oxide film sensor electrodes 104 and the reference electrodes 106.

Figure 3:
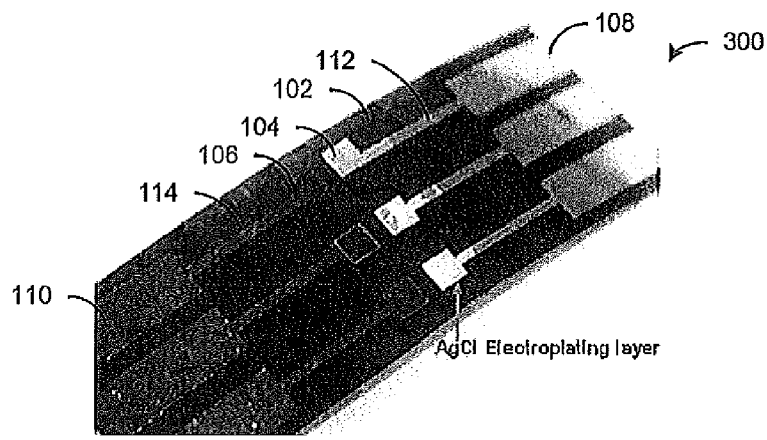
FIG. 3 is a photo of an array of pH sensors in accordance with another embodiment of the present invention.
Figure 4:
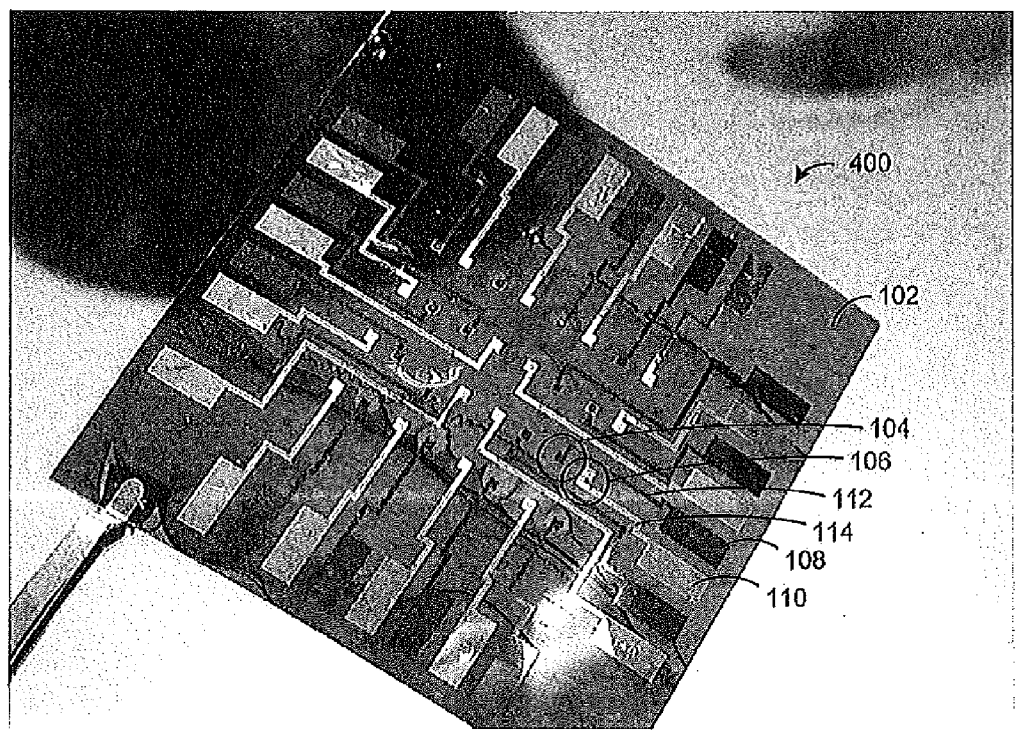
FIG. 4 is a photo of an array of pH sensors in accordance with another embodiment of the present invention.

Note that the present invention is not limited to the specific orientation shown in FIG. 2, Moreover, FIG. 2 is not to scale. As a result, any suitable orientation of the components can be used, and the components can be of any suitable geometric shape. For example FIGS. 3 and 4 are photos of two different types of pH sensor arrays 300 and 400 in accordance with additional embodiments of the present invention.

Now referring to FIGS. 5A-5F, a method 500 for fabricating a pH sensor in accordance with another embodiment of the present invention is shown. More specifically FIG. 5A shows the Cr and Au deposition on a Kapton polyimide substrate 102, FIG. 5B shows the SU-8-100 deposition for the sacrificial layer, FIG. 5C shows the $IrCl_4$ sob-gel process, FIG. 5D shows the thermal treatment, FIG. 5E shows the Cr, Pt and Ag deposition and FIG. 5F shows the AgCl electroplating.

The pH sensor 100 was fabricated by standard photolithography and lift-off processes. All metal layers were deposited by electron-beam evaporation. First, a layer of 7-nm thick Cr was deposited on a piece of Kapton polyimide substrate 102, followed by a 0.1-µm thick layer of Au. Iridium oxide sensing film was formed by the sol-gel process [30] which will be discussed in more detail below. 7-nm thick Cr and 3-nm thick Pt were evaporated for adhesion. A 30-nm thick silver layer then was deposited by electron-beam evaporation. Silver chloride (AgCl) reference electrodes were formed by electroplating. IN this particular example, the working and reference electrode areas were 2×2 mm².

The Sol-gel process will now be described. $IrO_x$ films were selectively deposited with sol-gel processes onto the gold electrodes. The electrodes were exposed through small windows in the SU-8 sacrificial layer, as shown in FIG. 5B. The sol-gel coating solution was based on the recipe described in [30]. One gram of anhydrous iridium chloride ($IrCl_4$) was dissolved in 42 ml of ethanol ($C_2H_5OH$). 10 ml of acetic acid ($CH_3COOH$) was added in the solution. The coating solution was stirred by a magnetic rod for one hour.

Thin film was formed by clip coating at a 2.0-cm/min withdrawing rate in the solution. After dip coating, the sample was thermally treated with a heating profile starting at 25° C. to 300° C. in a 2-hour period. The temperature stayed at 300° C. for 5 hours. To obtain amorphous iridium oxide film, the surface needs to be heated at or above 300° C. [30-32]. The furnace was then cooled clown in a 10-hour period to 25° C. FIGS. 6A-B show the morphology of the $IrO_x$ surface at peak treatment temperatures of 300° C. (amorphous) (FIG. 6A) and 550° C. (crystalline) (FIG. 6B) using the ZEISS Supra 55 VP scanning electron microscope (SEM). At 300° C., an amorphous surface was formed without cracks. As can be seen in FIG. 6A, the surface is uniform and smooth, even at the boundaries to the gold layer where cracks form often due to thermal treatment. The iridium oxide thin film crystallized at 550° C. [31] and the surface cracked at multiple places across the film, as shown in FIG. 6B. For the pH sensor applications, a uniform film surface is required. After experimenting at different temperatures, the 300° C. heat treatment was shown to provide good film quality.

Figure 7A:
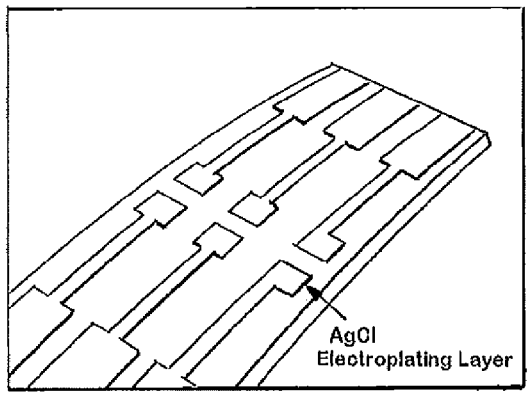
FIGS. 7A-7B are photos showing the AgCl electroplating layer before and after the KCl saturation process, respectively in accordance with another embodiment of the present invention.
Figure 7B:
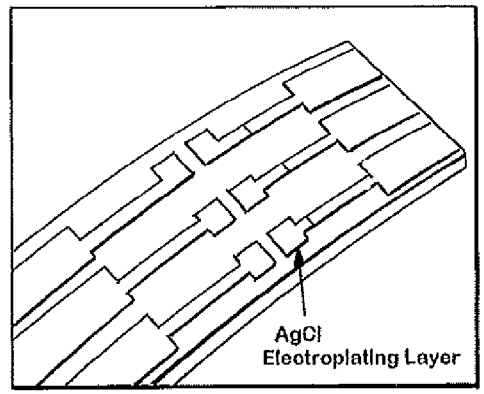

The electroplating process of the AgCl layer will now be described. An electrochemical anodization process was used on an anodic silver electrode with a platinum cathode electrode in 0.1-M HCl solution. An electrical current of 0.5 mA was applied on electrodes in HCl solution for 5 seconds. During the electrolysis, a brown silver chloride layer was formed on the silver surface as shown in FIG. 7A. The electrode surface was rinsed by DI water and then immersed in 3-M KCl solution for 24 hours to saturate and stabilize potentials [45]. FIG. 7B shows the electrodes after the saturation process.

Figure 8:
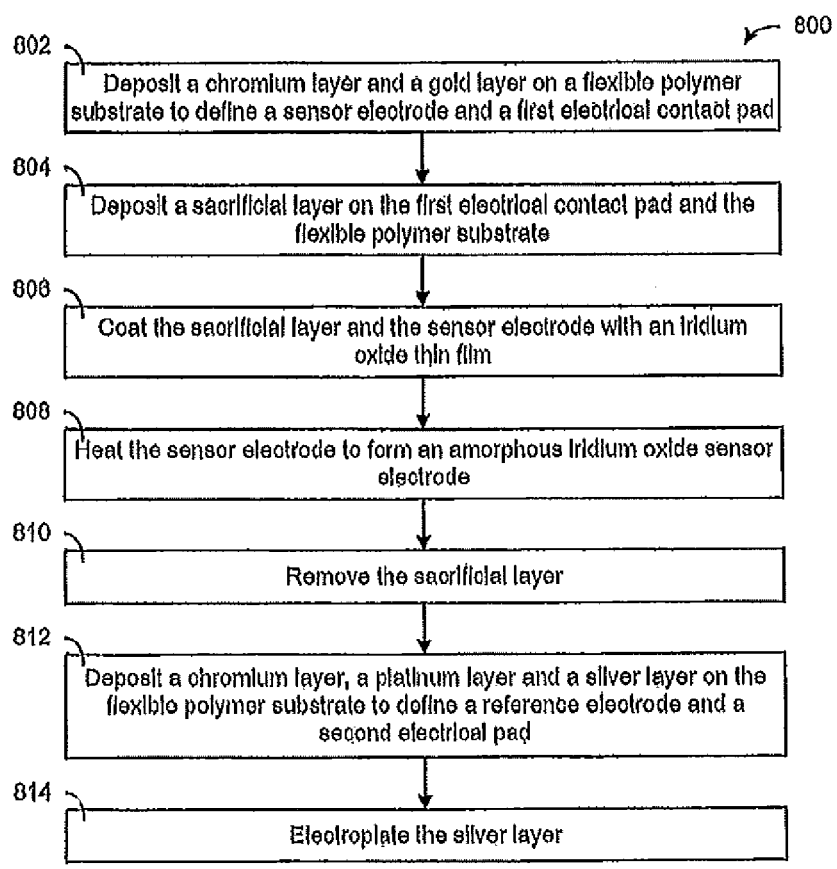
FIG. 8 is a flowchart of a fabrication process for the pH sensor in accordance with another embodiment of the present invention.

Now referring to FIG. 8, a flowchart of a fabrication process 800 for the pH sensor in accordance with another embodiment of the present invention is shown. A chromium layer and a gold layer are deposited (e.g., electron-beam evaporator, etc.) on a flexible polymer substrate, such as a Kapton polyimide flexible substrate or other suitable material, to define a sensor electrode and a first electrical contact pad in block 802. A sacrificial layer, such as SU-8 or other suitable material, is deposited on the first electrical contact pad and the flexible polymer substrate in block 804. The sacrificial layer and the sensor electrode are coated (e.g., dipcoating process, etc.) with an iridium oxide thin film in block 806. The sensor electrode is heated to form an amorphous iridium oxide sensor electrode in block 808. The sacrificial layer is removed in block 810. A chromium layer, a platinum layer and a silver layer are deposited (e.g., electron-beam evaporator, etc.) on the flexible polymer substrate to define a reference electrode and a second electrical pad in block 812, and the silver layer is electroplated in block 814.

Additional steps may include applying a sacrificial layer of S1813 to the chromium, platinum and silver layers; followed by the removal of the sacrificial layer of S1813. Note that the heating step can be at 150 degrees Celsius for at least 1 hour followed by a second heating step of 300 degrees Celsius for another 5 hours after the sacrificial layer is removed. The second heating step is performing in an oven purged with inert gas starting at 25 degrees Celsius and increasing to 300 degrees Celsius in a period of 2 hours, and staying at 300 degrees Celsius for another 5 hours. The step of depositing the sacrificial layer may include the steps of (a) depositing the sacrificial layer using a spin cycle, (b) heating the sacrificial layer at 65 degrees Celsius for 3 minutes and then 10 minutes at 95 degrees Celsius, and (c) developing and drying the sacrificial layer.

Figure 9:
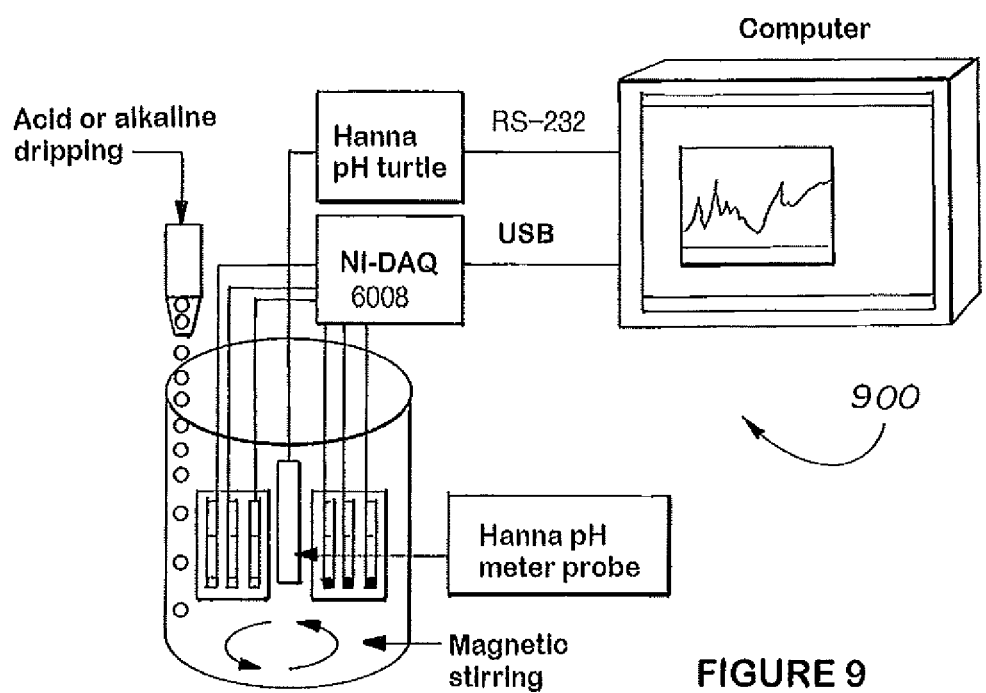
FIG. 9 illustrates a measurement setup to test the pH sensor in accordance with another embodiment of the present invention.

Referring now to FIG. 9, a measurement setup 900 to test the pH sensor is shown. A NI-DAQ 6008 USB card with a LabVIEW program was used for analog potential recording. A commercial Hanna pH sensor was used to verify the pH values of solution. The pH sensor array was clipped by a flat gator clamp and connected to the DAQ card. The pH sensor was immersed in acid or alkaline based diluted solution with a magnetic rod stirring at the bottom of the beaker. Hydrochloric acid and acetic acid were used for acidic tests while $NH_3$ and KOH solutions were used for alkaline tests. The Hanna pH sensor was placed in the test solution. The potential and pH values were displayed and recorded in a computer simultaneously.

Three possible mechanisms have been proposed for pH dependent redox equilibrium between two oxidation states of the iridium oxide [46] as $$Ir_2O_3 + 6H^+ + 6e^- \leftrightarrow 2Ir + 3H_2O \quad (1)$$

$$IrO_2 + 4H^+ + 4e^- \leftrightarrow Ir + 2H_2O \quad (2)$$

$$2IrO_2 + 2H^+ + 2e^- \leftrightarrow Ir_2O_3 + H_2O \quad (3)$$

$$E = E^0 - 2.303 \frac{RT}{F} pH = E^o - 59.16\, pH \quad (4)$$

where:

$E^0$ is the standard electrode potential with a value of 926 mV;

F is the Faraday's constant with a value of 96,487 coul/equiv; and

R is the gas constant with a value of 8.314 joules/deg. RT/F is equal to 25.688 at 25° C. The pH potential sensitivity is 59 mV/pH if space charges are formed [22,46] which is called the Nernstian response. The pH sensitivity of our sensor is based on the super-Nernstian potential response [44] as the sensitivity will be higher than 59 mV/pH.

Figure 10A:
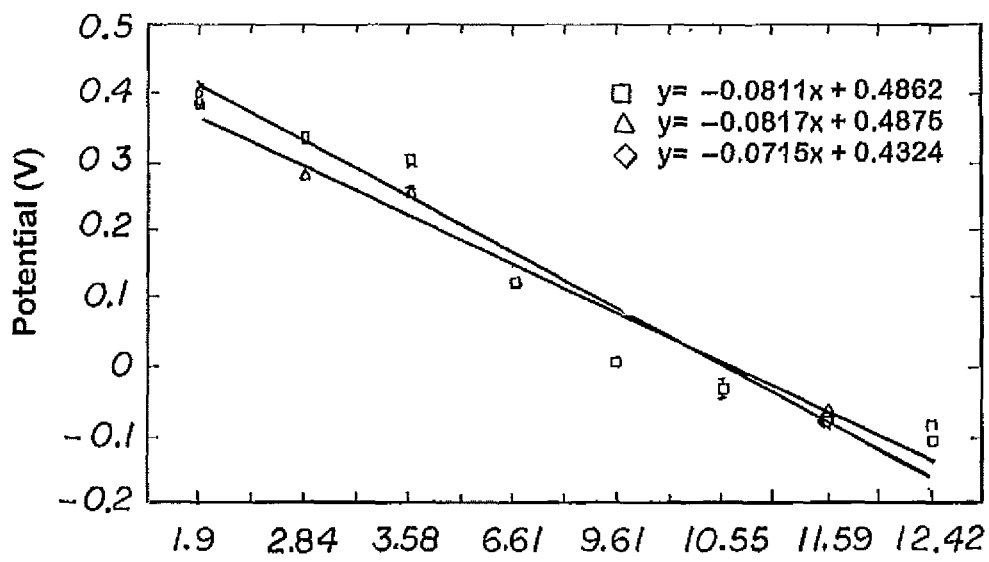
FIGS. 10A-10B are graphs illustrating the measured super-Nernstian potential responses in titration from pH=1.9 to pH=12.42 (FIG. 10A) and from pH=11.8 to pH=1.92 (FIG. 10B) in accordance with another embodiment of the present invention.
Figure 10B:
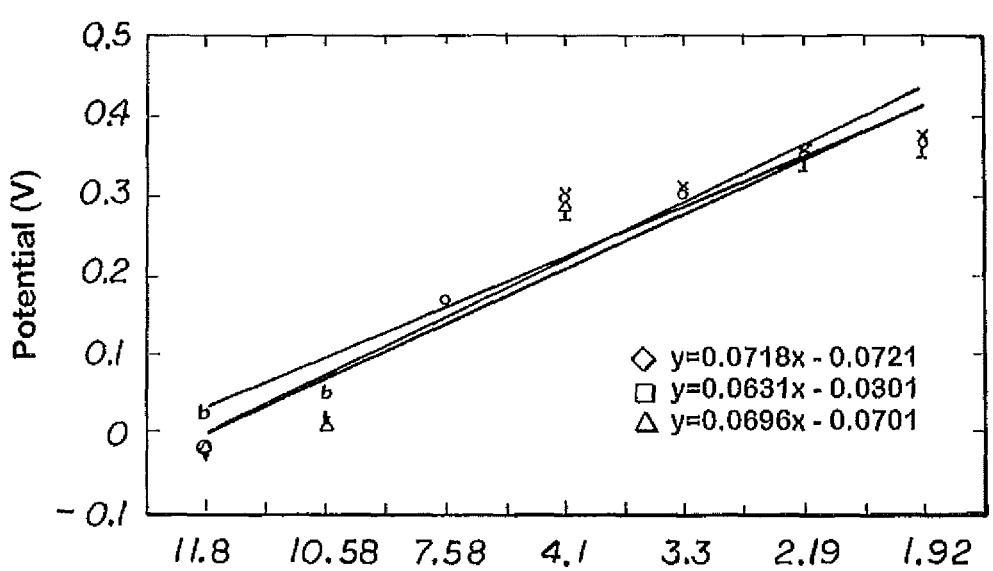

The sensitivity of $IrO_x$ pH sensor was validated by pH titration tests at the room temperature. DI water, HCl, and KOH were used during the titration. Three sensor electrodes in an array were used to demonstrate the linear super-Nernstian response. FIG. 10A shows the potential responses with eight different pH levels from 1.9 to 12.42 as KOH was dripped in the diluted HCl solution for titration. The results showed sensitivity ranging from −71.5 mV/pH to −81.7 mV/pH [43]. FIG. 10B shows the potential responses with seven different pH levels from 11.8 to 1.92 resulting in sensitivity between −69.6 mV/pH and −71.8 mV/pH as HCl was dripped in diluted KOH solution for titration. The different sensitivities may be caused by the state of oxide [49]. The sensitivity of IrOx increases when the oxidation state reduces. A higher potential coincided with a high valence oxide and vice versa [49]. During the tests, our pH electrode array on flexible substrate showed higher sensitivity, compared to the electrode formed by other methods which typically have sensitivities in the range of 55-70 mV/pH [22, 47-48].

The response time of the pH sensor was measured in three different tests. The first test was from the acid to alkaline condition by quickly dripping 0.1M KOH into an acidic solution where the sensor was. The second one was from alkaline to acid by quickly dripping 0.1M HCl into an alkaline solution with the sensor in the solution. The third one was tested by dripping diluted HCl droplets directly on the dry sensing electrode surface of the sensor. The response time of pH electrodes is defined as the time needed for the potential change to reach 90% within the equilibrium value of potential [22].

Figure 11A:
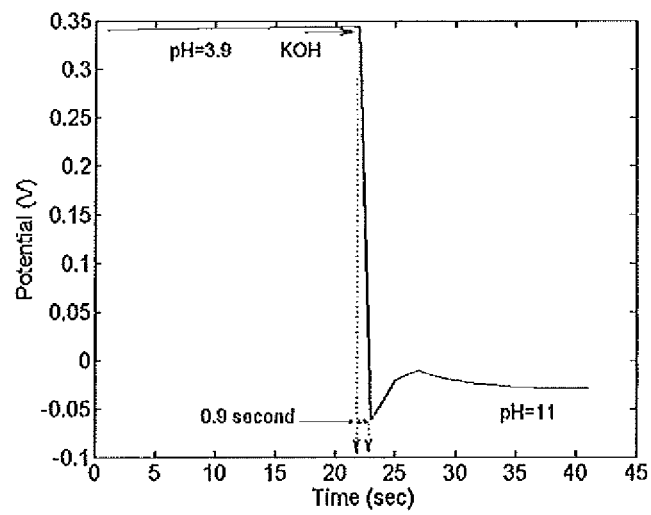
FIGS. 11A-11C are graphs showing results for response-time tests in accordance with another embodiment of the present invention.
Figure 11B:
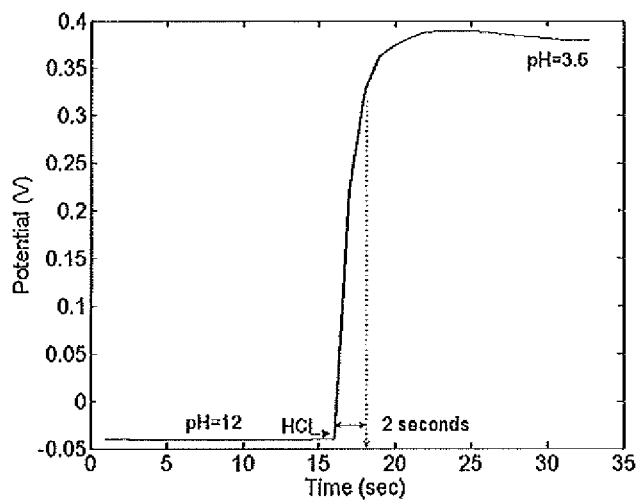
Figure 11C:
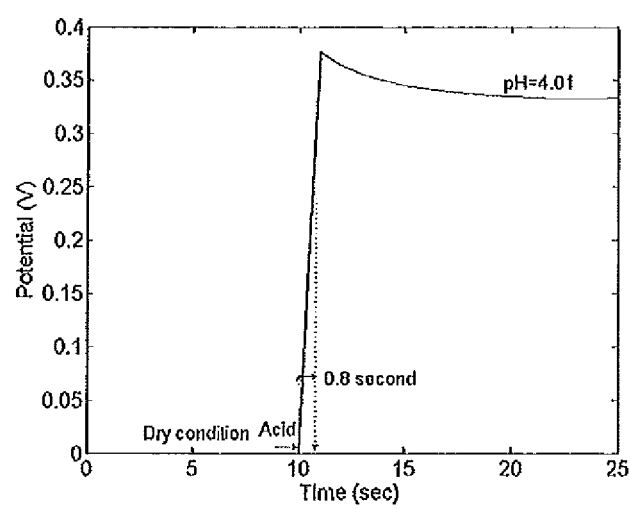

FIG. 11 shows typical results for the response-time tests. FIG. 11(a) shows a response time of 0.9 second with a measured potential step change in our flexible pH electrode from pH=3.9 to 11. FIG. 11(b) shows the result from pH=12 to 3.5. The response time is about 2 seconds. In both tests, the pH values of the solutions were verified 15 seconds after the events by the commercial pH sensor (HANNA Instruments) in the beaker since the reading of the HANNA sensor also varied with time. FIG. 11(c) shows the result from the dry surface condition to pH=4.01. The response time is about 0.8 second. After ten similar experiments were conducted, we concluded that our flexible pH sensor responds within 2 seconds.

Compared with the response times of 5-15 seconds reported in literatures [57-58], the response time of our $IrO_x$ flexible pH sensor was shorter and consistent with different pH level changes. This may be due to the better quality of the $IrO_x$ film with appropriate coating and annealing processes in our sol-gel fabrication, as suggested by Olthuis et al [49] that the response time is mostly affected by the porous properties of the sensing film. The bulk pH solution needs to equilibrate the liquid in the pores of iridium oxide film in which the process increases the response time. Thus, although our sol-gel $IrO_x$ film has lower porosity, which provides less sensitivity than porous AIROF and SIROF, the sensor responds quicker.

The reversibility and repeatability tests of $IrO_x$ pH sensor were performed to evaluate the need for frequent recalibration that is required for many pH sensors [51].

To demonstrate reversibility, our sensor was tested in a pH titrated cycle with pH=1.5 to pH=13.1 and back to pH=1.5 continuously without cleaning and drying the surface of electrode. During the titration process, KOH or HCl was dripped into the base solution in order to increase or decrease the pH level of the base solution. The commercial pH electrode (HI98128, HANNA Instruments) was used to reference the pH values of the titrated base solution. The one-time reading from the HANNA sensor was taken 10 seconds after the titration event. The titration and measurement cycles were repeated three times, and the results were plotted with the cycles overlapped in FIG. 12. The distinct and constant potentials clearly responded and recognized eight different pH levels in a complete titration cycle (See FIG. 13).

Figure 14:
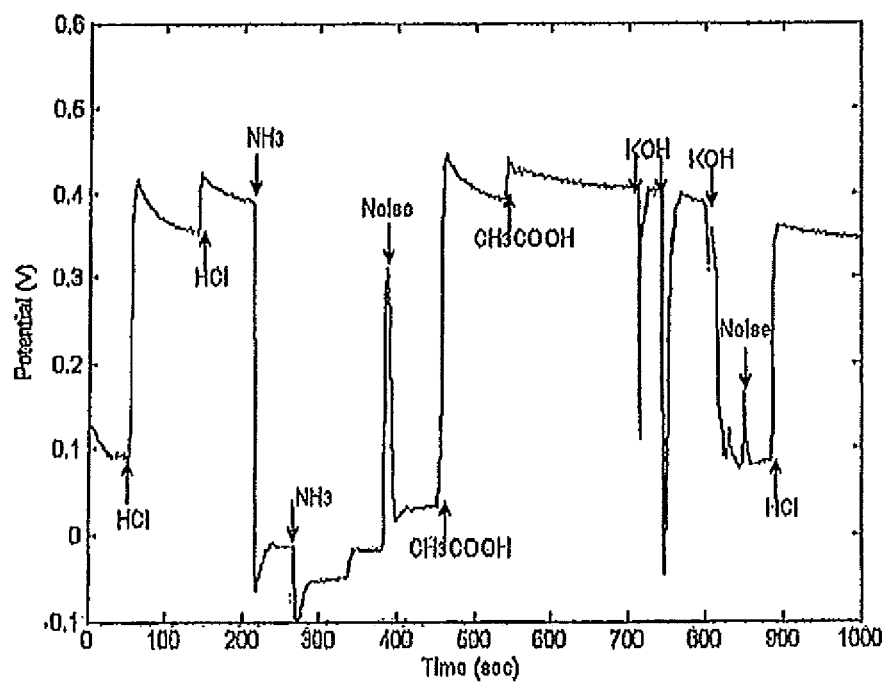
FIG. 14 is a graph showing the selectivity tests with different acidic and alkaline solutions in accordance with another embodiment of the present invention.

Two different acidic solutions HCl and $CH_3COOH$ and two different alkaline solutions KOH and $NH_3$ were used for selectivity tests. Random amounts of these acidic or alkaline solutions were dripped into the beaker in which the solution was stirred by a magnetic rod. The results are shown in FIG. 14. The potentials followed the pH values independently with the different types of solutions. The detected potential responded quickly to the added solution as it was dripped near the sensor electrode. As the added solution was stirred into the base solution, the potential slowly changed. In this test, noises of potential happened due to the disturbance of solutions by the stirring rod. The IROF sensor responded to pH variations, independent of titration solutions, showing specificity to only pH values.

Figure 15:
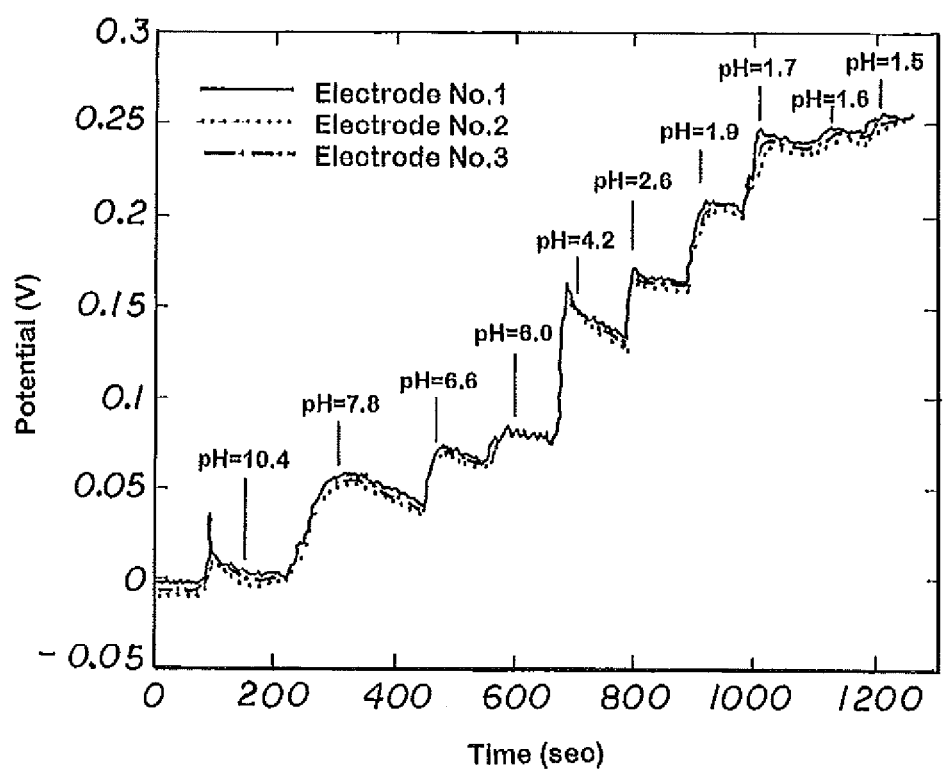
FIG. 15 is a graph showing the potential responses of the pH sensor array in accordance with another embodiment of the present invention.

FIG. 15 shows the potential responses of the $IrO_x$ electrodes in a series of different pH levels. Three sensors in an array were tested simultaneously in the same titration beaker. The diluted KOH solution was titrated by 1M of HCl dripping from pH=10.4 to 1.5. The pH values were recorded by the Hanna pH sensor. During the test, the $IrO_x$ pH sensor potentials followed the pH values coordinately from −0.01V to 0.25V, and kept stable in each pH step. Three electrodes in the array behaved similarly with little difference. The difference in potentials may be due to the difference in locations of electrodes with respect to the titration solution HCl dripping location in the beaker. In addition, another potential drift phenomenon happened in each titration event. When acid was dripped into the beaker, the potential indicating the respective pH level jumped to a certain value, but then started to reduce and stabilize slowly until the next titration event. This potential drifting in each titration step might be introduced by the oxidized state also described by Olthuis et al [49].

Figure 16A:
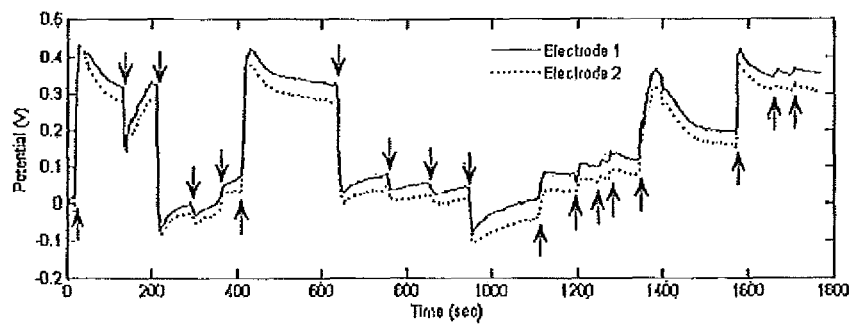
FIGS. 16A-16B are graphs showing the dynamic pH titration test results in accordance with another embodiment of the present invention.
Figure 16B:
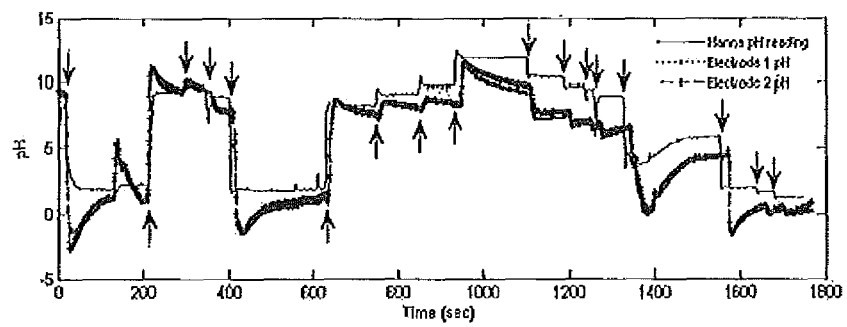

In a pseudo-random titration experiment, we used two $IrO_x$ electrodes that were fabricated in different batches. Both electrodes have been used in many titration tests and aged one month. The pH levels were varied by dripping random acidic or alkaline solutions into a beaker. FIG. 16A shows the time-lapsed record of the measured potentials from two different electrodes. The arrows indicate the titration event. FIG. 16B compares the pH values derived from the measured electrode potentials with the pH values measured by the Hanna pH sensor. The changes of potentials corresponded to the pH variations of the solution instantly and repeatedly during the random titration process. The results showed potential drifts at the same pH values that were detected by the Hanna pH sensor. Assuming the Hanna pH sensor did not drift, the observed phenomenon may be caused by the following reasons: (1) since during titration acid or alkaline solutions were dripped into deionized water which had very low ion concentration, the ion source in the beaker mainly was from the titration solutions. The ion concentration varied and redistributed with time even the pH values were the same. The localized ion concentrations detected by the IROF electrodes then varied. The Hanna sensor has a large sensing area so it may be sensitive to local ion concentration variation. (2) Mentioned previously, the drifting problem may be caused by the different oxidation states [49] on the film. Besides the potential drifts, the two sensors from two different fabrication batches produced slightly different potential levels at the same titration section. The phenomenon may be caused by the chloride ions that were not fully removed from the coating surface during the annealing process [50] and different oxidation stages since they were fabricated at different times. Despite these factors, our iridium oxide sensors clearly indicated the random pH variations of the solution.

Figure 17A:
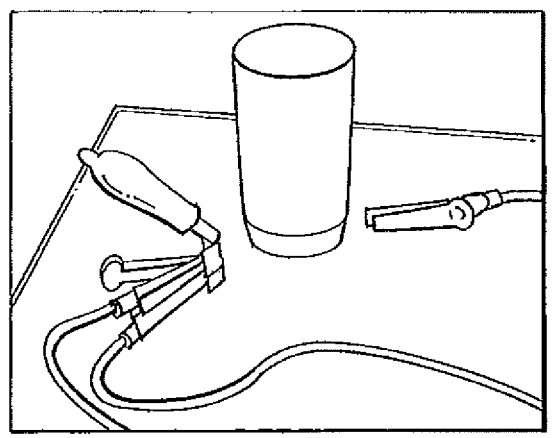
FIGS. 17A-17B are a photo (FIG. 16A) and a diagram (FIG. 16B) of a setup configuration for the tube test in accordance with another embodiment of the present invention.
Figure 17B:
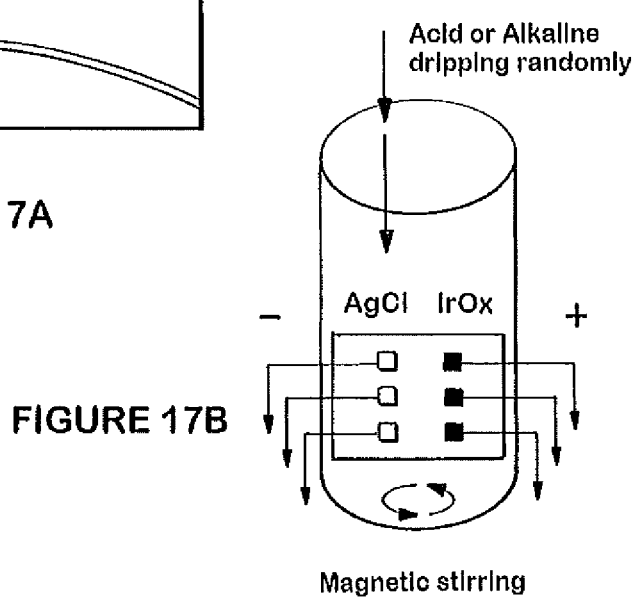
Figure 18:
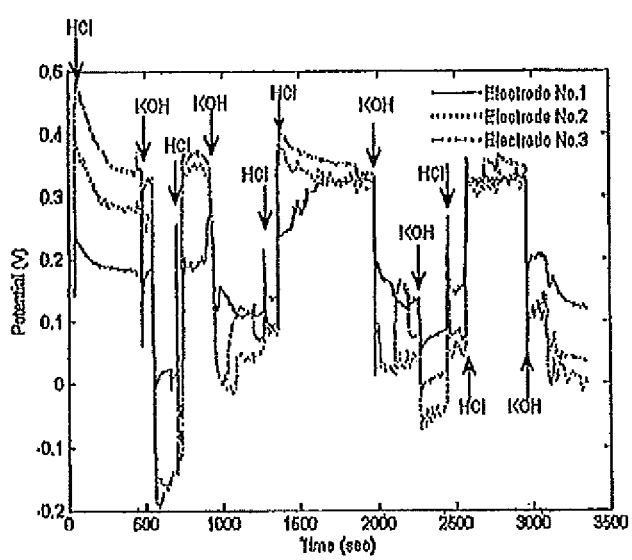
FIG. 18 is a graph showing the potential responses of the flexible sensors inside a small tube in accordance with another embodiment of the present invention.

A sensor in accordance with the present invention can be used for the reflux detection in human esophagus [52] for which the flexible sensor needs to fit into a small confined space where it is difficult to use convention glass electrode pH sensors as described in provisional patent application No. 61/349,281. In FIG. 17A, our IrO$_x$ pH sensor array was bent and inserted into a long tube with a diameter of 2 cm. The tube was filled with pH=7 DI water first, then 0.1-M KOH and 1-M HCl were dripped pseudo-randomly into the tube. A magnetic stirrer was used at the bottom of the tube as shown in FIG. 17B to mix the solution. The sensor electrode array was arranged vertically. The array has three electrodes with a spacing of 3 mm between them giving a spatial resolution of 3 mm for localized pH sensing. Due to the small tube diameter, the commercial Hanna pH sensor was not able to be placed inside the tube to measure the pH values. FIG. 18 shows the potential changes with pseudo-random drips of acidic or alkaline solutions. The potential variations in each electrode responded to the titration quickly and coordinately. With the electrode #3 at the top and the electrode #1 at the bottom, the potential peak values of the electrode #3 were always higher than those from the electrode #1. This again was due to the spatial distributions of the ion concentrations. This phenomenon was more obvious in the beginning of the experiment when HCl was first added into the deionized water. As more titration solutions were added, more ions existed in the tube and so the differences of potentials among three electrodes became less. The sensor electrodes locally detected the potentials from the pH dependent redox equilibrium. With calibration of the initial conditions on the electrodes in an array, the sensor array can provide time-lapsed spatial information of pH values.

The present invention, therefore, provides an iridium oxide film based pH sensor on a flexible polyimide substrate that provides the advantages of lower costs, simpler processes and improved device flexibility. Some additional uses of the iridium oxide film based pH sensor in accordance with the present invention as a passive wireless RFID detector will now be described. Note that other uses that are not specifically described herein, such as active wireless RFID detectors, are within the scope of the present invention.

Figure 19:
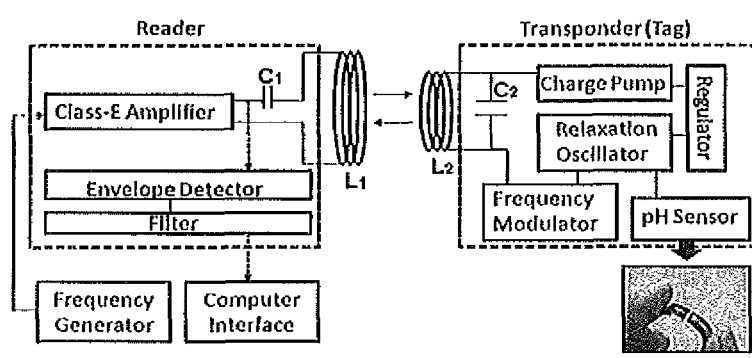
FIG. 19 is a block diagram in accordance with another embodiment of the present invention.

The present invention can also be used as a wireless pH sensor. The wireless pH sensing system of the present invention includes a passive transponder (tag) embedded with our flexible iridium oxide pH sensing electrodes, and a reader. The batteryless operation relies on the inducting coupling between reader and tag coils antennas with tuning capacitors at a resonant frequency. The operation principle is similar to the one in a RFID. FIG. 19 shows the blocks diagram of the wireless pH sensor system.

Figure 20:
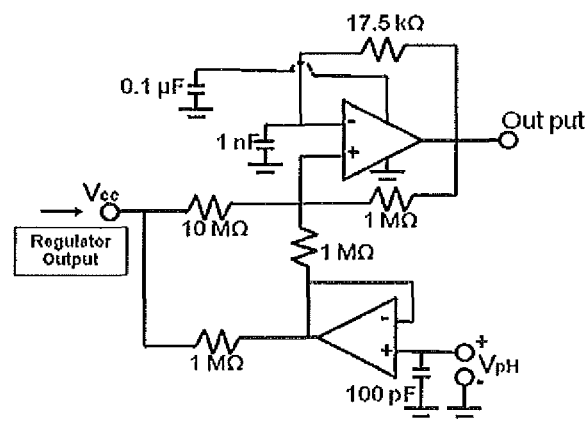
FIG. 20 is a oscillator diagram in accordance with another embodiment of the present invention.

The transponder of the passive wireless pH sensor system consists of a voltage multiplier or charge pump [59], a relaxation oscillator [60], and a frequency modulator. The antenna inductor ($L_2$) and a capacitor ($C_2$) form a resonant circuit which receives RF powers from the reader. The voltage multiplier consists of diodes and capacitors amplifying the voltage from hundreds of millivolts to volts. A voltage regulator was utilized to limit the output voltage at 2.5V. The relaxation oscillator converts the electrochemical potentials generated by the pH electrodes to frequency-varying signals which are based on the voltage level at the input of the comparator [60], as shown in FIG. 20. The sensor signals then drive a frequency modulator to modulate the carrier signals back to the reader antenna. In our design, the modulated frequency decreases from 22 kHz to 15.9 kHz responding to the pH level from 2 to 12.

The carrier frequency of the wireless pH sensor was tuned at the resonant frequency of 1.3 MHz. The reader and tag coil antennas have dimensions of 9×12 cm$^2$ and 23×8.5 mm$^2$. Both the reader and tag were fabricated and assembled on printed circuit boards for demonstration purpose. The coil antenna wire in the tag was wrapped around the printed circuit board while the reader coil was wrapped around a plastic frame, connecting to the reader circuit board with wires, as a handheld antenna. A DC power supply of 8V provides a 400-mA current to the reader. With the coil antennas facing each other in parallel, a communication distance of 10 cm in air was achieved with a signal-to-noise ratio of 18 dB at the modulated frequencies between 16 and 22 kHz. The frequency shills could be detected clearly and repeated in the computer with a 1-Hz sampling rate. When the distance increased to 12 cm, the signal-to-noise dropped to 14 dB and the peak frequency has a frequency jitter less than 50 Hz. The reader frequency counter was not able to count the frequency reliably when the distance increased to 16 cm as the tag did not receive sufficient energy from the reader to power up the integrated circuits in the tag.

To test the sensitivity, a flexible pH sensor was connected to the batteryless tag circuit, as shown in FIG. 19. The potential output modulated the frequency of the relaxation oscillator in the range of 16-22 kHz. The demodulated frequency signals at the reader were recorded in computer with a LabView-based program and verified by an Agilent E4403B spectrum analyzer. Buffer solutions with pH=2, 4, 7, 10, and 12 were used to measure the sensitivity. Both the electrochemical potentials at the sensor electrodes and the wirelessly detected frequencies were measured and recorded simultaneously. The sensor was washed by DI water and dried by compressed air between tests.

Figure 21:
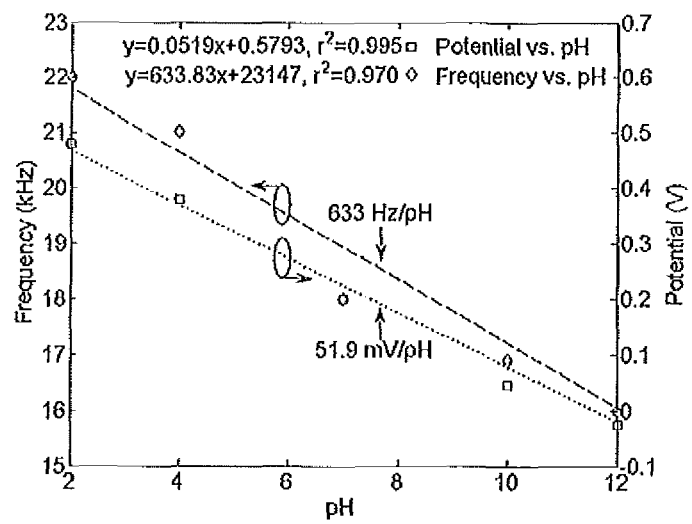
FIG. 21 is a graph showing the sensitivity of the wireless pH sensor in accordance with another embodiment of the invention.

FIG. 21 shows that the potential and frequency responses between pH=2 and pH=12. The result shows a sensitivity of −51.9 mV/pH with a correlation coefficient $r^2$=0.99 for the tested electrodes, which is also a near-Nernstian response. The sensitivity of the wireless pH sensor system in term of modulated frequency is −633 Hz/pH with a correlation coefficient $r^2$=0.99. The result shows that the system is able to transduce the pH potential wirelessly. The sensitivity in frequency is sufficient since the sampling rate to record the pH value in the computer is 1 Hz.

Figure 22:
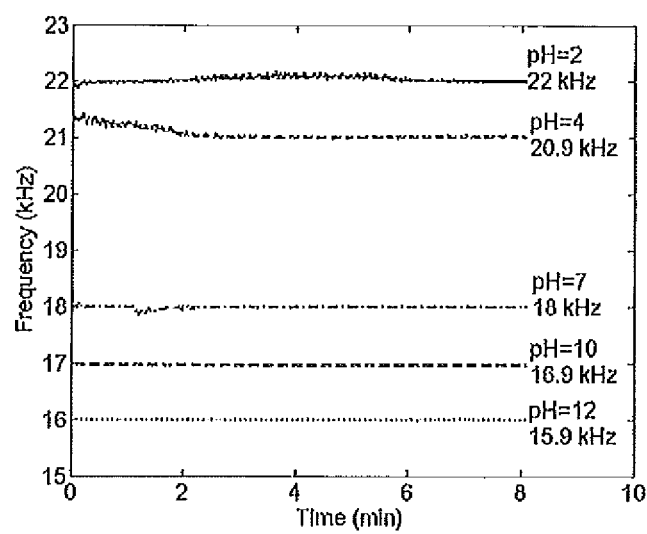
FIG. 22 is a graph showing stability results of the wireless pH sensor in accordance with another embodiment of the invention.

Stability tests were conducted with the wireless pH sensor system at pH=2, 4, 7, 10 and 12. Each buffer solution was dripped on the sensor electrodes for 8 minutes. The sensor was then cleaned and dried after each test. The responding frequencies were recorded continuously. FIG. 22 shows the frequency responses at five different pH levels. The modulated frequencies stay stable at 22, 20.9, 18, 16.9, and 15.9 kHz corresponding to the pH level at 2, 4, 7, 10, and 12, as expected. The wireless pH sensor system was able to transduce the sensor signals stably. For pH=7, 10, and 12, the frequency drifts were negligible. The noises occurred at pH=2 and pH=4 were caused by the shaking of the sensor during test in which the solution drop encountered localized mixing on top of the electrodes. The drift occurred for the pH=4 case was due to the contact of liquid onto the electrodes as the drop was unevenly dripped on the surface. It took about 2 minutes for the drop of liquid to reach equilibrium to provide stable potential between the $IrO_x$ and AgCl electrodes. This event shows that the sensor is sensitive enough to detect the non-uniform ion distributions in a drop of liquid. In the stability test, it was obvious that when the potentials reached their stable values, the modulated frequencies would stay constant without drifts.

Figure 23:
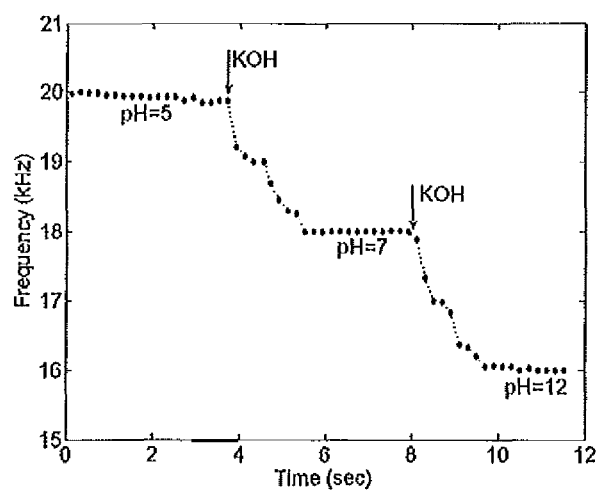
FIG. 23 is a graph showing results for titration responses in accordance with another embodiment of the invention.

The titration performance of the wireless pH sensor system was tested in a continuous titration process at three pH levels of 5, 7 and 12. The result is shown in FIG. 23 with a sampling rate of 5 Hz. Test solution of pH=5 was dripped on the sensing electrodes, after 4 seconds KOH solution was dripped in the pH=5 solution. The alkalinity raised the pH level to 7, verified by the HANNA pH meter. It took about 1 s for the ion distribution in the liquid to reach equilibrium during which the HANNA pH meter also gave scattered readings indicating that the pH values were not stable in the liquid. After the frequency stabilized, the same process was repeated and the pH level increased to 12. The sensor was used continuously without cleaning between titration steps. The sensor system responded quickly and distinctly to pH value variations indicating the response time for both the sensor electrodes and the wireless transponder system is sufficiently short for real-time monitoring.

The present invention can be used to detect spoilage of food (e.g., meat, fish, etc.) The pH sensors on flexible substrates can be used in monitoring pH values in food processes in food industry, chemical processes in pharmacy and material supplier industry and biochemical reaction monitoring in medical applications. In applications targeting for supermarket and food supply chain industries, the freshness of meat and fish is monitored using the flexible iridium oxide pH sensor. The packages will require miniature flexible sensor that is biocompatible. The sensor has to be miniature and flexible so it can be embedded with a RFID chip inside a plastic label. The flexibility of sensor will allow the sensor to conform to the surface of the meats or fishes packaged. The sensor electrode has to be biocompatible and safe since it will be touching the food until it is consumed. The sensor device architecture should also allow integration with existing RFID communication methods.

Figure 24:
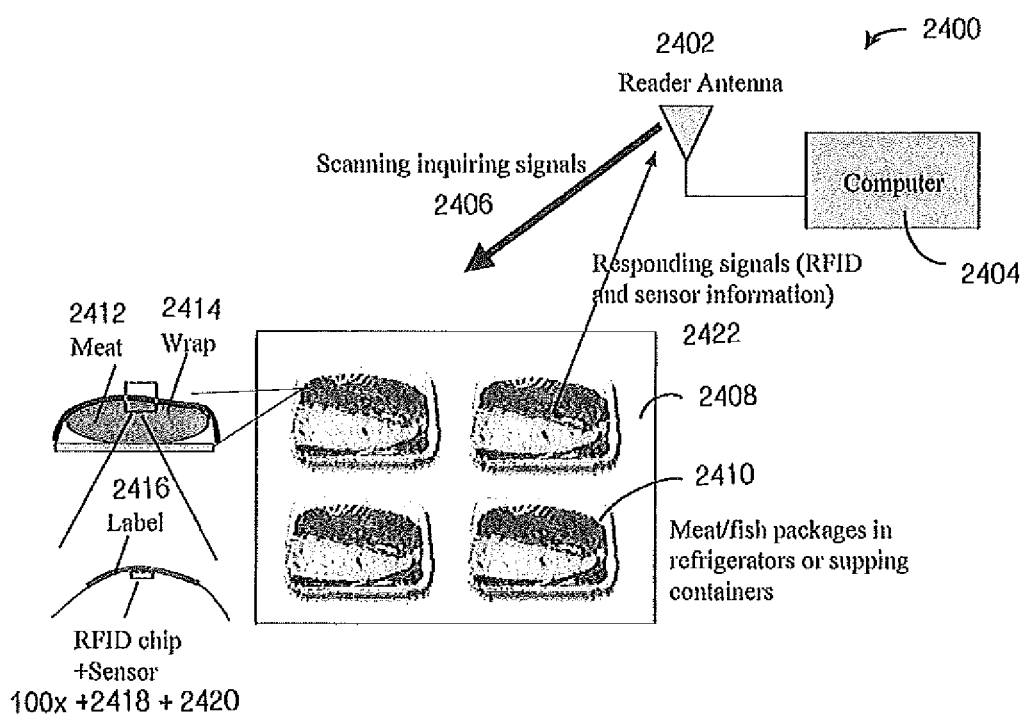
FIG. 24 illustrates a food freshness monitoring system in accordance with another embodiment of the present invention.

For example, the present invention provides a packaging system for meat and fish in retailer supermarkets or supply chains. The system 2400 shown in FIG. 24 includes packages consists of RFID senso-embedded plastic wrappers and RFID readers. A reader antenna 2402 connected to a computer 2404 sends out RFID inquiring radio-frequency signals 2406 to the storage area 2408. Each package 2410 contains meat or fish 2412 wrapped by a plastic wrapper 2414. Inside the wrapper 2414, a label 2416 facing outside and showing information (barcode, nutrition information, price, expiration date and etc) about the package 2410 has an embedded sensor 100 or sensor array 100x, a RFID chip 2418 and a tag antenna 2420 inside. The sensor 100x touching the meat or fish 2412 can sense the pH value. When the inquiring RFID signal 2406 sent by the reader (2402+2404) is received by the tag antenna 2420 and the inquiring ID matches with the ID in the package chip 2418, the chip 2418 harvests the received radio-frequency signal powers 2406 and uses the powers to drive the sensor 100x to detect pH value of the meat/fish 2412. The RFID chip 2418 then sends out the RFID and sensor information (collectively 2422) back to the reader (2402+2404). Note that a visual indicator could be added to the exterior of the package 2410 to indicate the pH of the food.

Using this sensor-embedded RFID method, it does not require workers to check individual packages manually for freshness of meats or fishes which is time and effort consuming. The freshness information can be obtained remotely by a computer and monitored continuously. Each package RFID also contains packaging and expiration dates so the computer can flag alerts when the packages are about to expire.

The relationship between the meat/fish freshness and pH changes has been investigated. After livestock is killed, the oxygen stops to deliver into muscle which induces several different biochemical reaction changes. These changes contribute various meat flavors and stages of spoilage. Generally speaking, meat property variations follow three steps:

Step 1—Rigor Mortis (pH Reduces)

Because of the lack of oxygen in the dead muscle, the glycogen will be decomposed and become the lactic acid. On the other hand, the Adenosine Tri Phosphate (ATP) is hydrolyzed to be phosphoric acid too. The pH level of the muscle group will reduce, and muscle becomes hard. We call the phenomenon "Rigor Mortis".

Step 2—Autolysis (pH Slightly Increases)

After the rigor mortis, the muscle will be dissolved to become the smaller molecule by enzyme. The muscle will become much softer as called off-rigor. The protein in the dead muscle also dissolves to be the amino acid which includes different types of structure ex. Amine. On this moment, the pH level of muscle group will increase.

Step 3—Spoilage (pH Increase)

With amino acid producing, some microbes start to grow and absorb the amino acid and proteins. There are different chemicals such as Indol, Scatol, ammonia, and sulfide created after the absorbing processes created by bacteria. The ammonia-based chemicals increase pH level of the meat/fish and bad odors.

As described above, the pH variations of food is related to spoilage. The transitions of acid-slight alkaline-alkaline could be used to identify the stages of meat spoilage. The IROF (iridium oxide film) based pH sensor in accordance with the present invention is use as the indicator to recognize the time line in the spoilage process. Testing of the sensor 100x will now be described.

Figure 25:
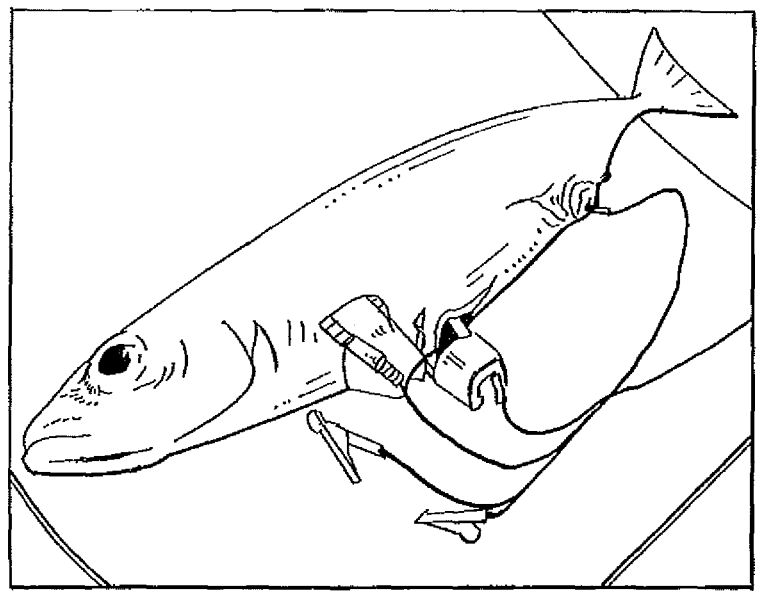
FIG. 25 is a photo of a mackerel spoilage test using IROF pH sensors in accordance with another embodiment of the present invention.
Figure 26:
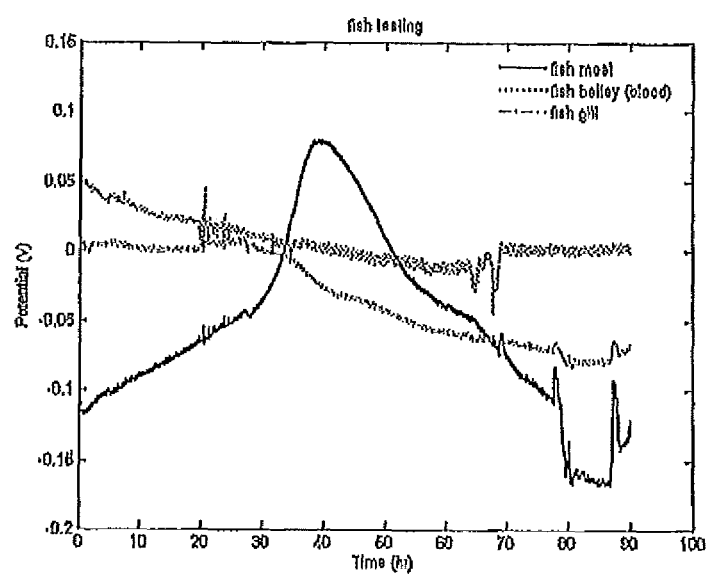
FIG. 26 is a graph depicting the test results of mackerel spoilage of FIG. 19.

Frozen whole-body mackerels were used as the test samples in the first test. Three individual iridium oxide sensors were placed in three different parts, which were belly, gill and muscle as shown in FIG. 25. The test was conducted at the room temperature of 25° C. for 90 hours. The potentials from the sensor electrodes were recorded continuously by a computer. FIG. 26 shows the time-lapsed results. The sensor showed clearly the sensor potential changes in the transition of alkaline-acid-alkaline on fish meat (muscle) section, while the gill and belly sections indicated acid to alkaline changes. The pH value transitions do not follow exactly the spoilage mentioned earlier, however, the pH changes do indicate the freshness changes. The fish started to emit odors after 30 hours indicating the fish became spoiled, as the measured pH value started to change significantly.

Figure 27:
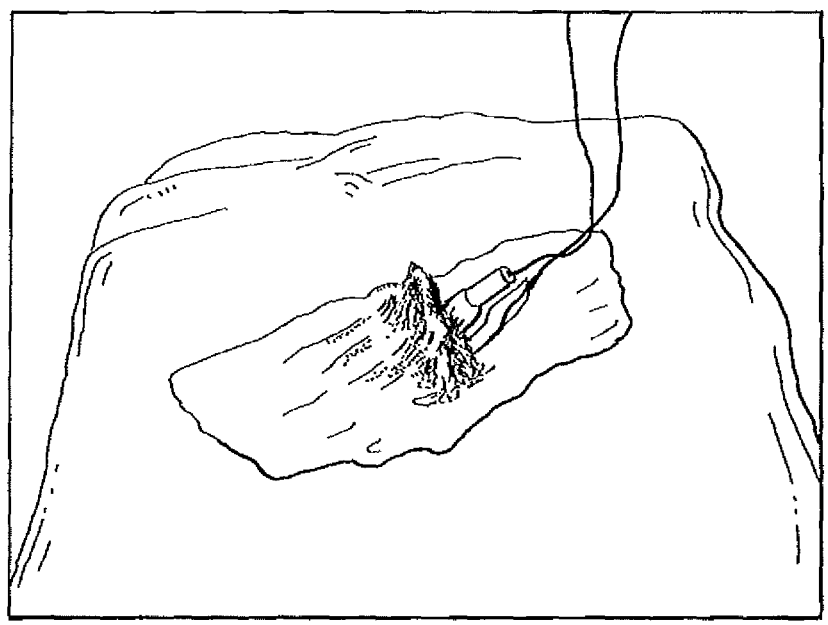
FIG. 27 is a photo of a tilapia fillet spoilage test with dry ice bags using IROF pH sensors in accordance with another embodiment of the present invention.
Figure 28A:
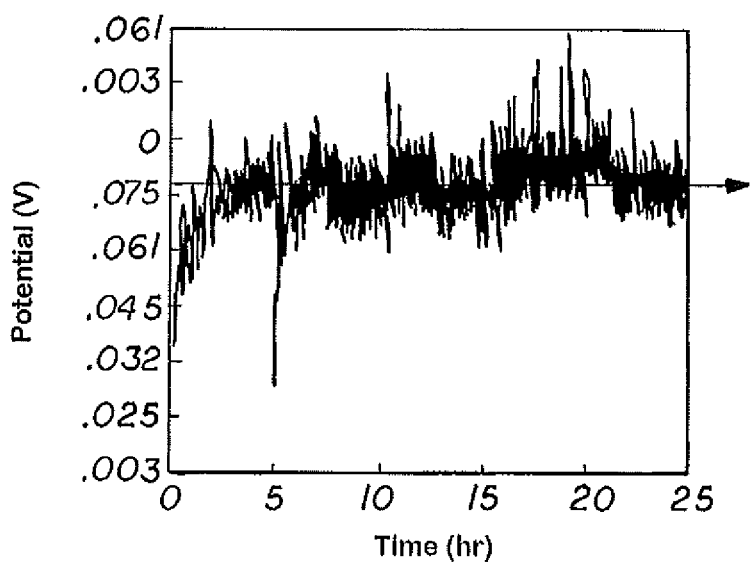
FIGS. 28A-28B are graphs depicting the test results of the tilapia fillet spoilage tests of FIG. 21 with dry ice bags (FIG. 22A) and without dry ice bags (FIG. 22B)
Figure 28B:
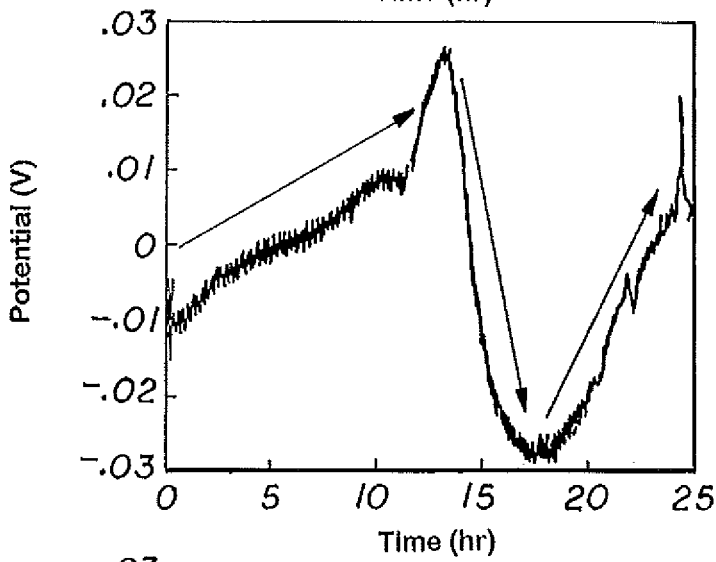

Next a tilapia fillet test was conducted that focused on comparison of the fish meat properties under different temperatures. One fillet was wrapped by the dry ice bags, as shown in FIG. 27, for 24 hours while the other fillet was tested at the room temperature of 25° C. The one at the room temperature should go spoiled quicker. The IROF pH sensors were inserted between flesh in the both samples. FIG. 28A shows the results after 24 hours. The one wrapped by the dry ice bags has no dramatic potential changes, which means the pH value kept constant around the same level. This may indicate that there were no microbes growing and no obvious odor was detected. However, the sensor inside the fillet without the dry ice bags wrapped has dramatic potential variations within the 24-hour period. The alkaline-acid-alkaline transition pattern was showed in FIG. 28B. The pH level changed probably because of the chemical reaction and microbes growing as mentioned before. An obvious odor was detected in this fillet.

Figure 29:
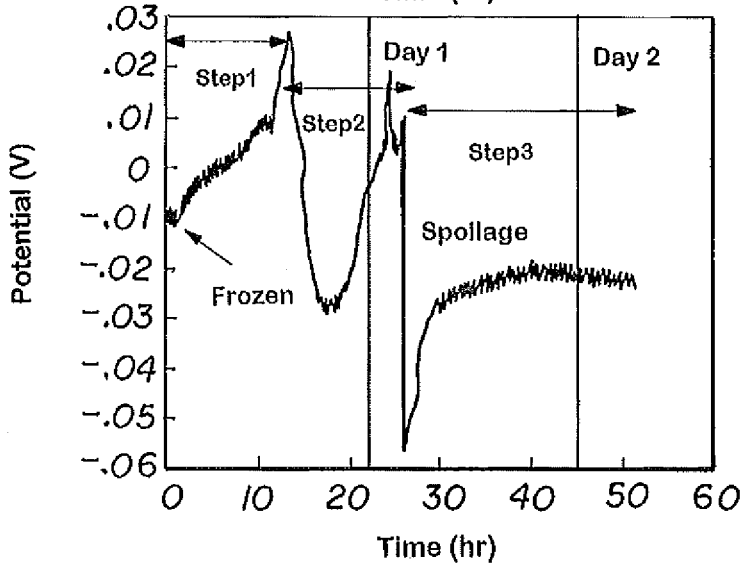
FIG. 29 is a graph showing the spoilage test results of the tilapia fillet (FIG. 21) within a 50-hour period.

FIG. 29 shows the spoilage test results of the tilapia fillet within a 50-hour period. There were clearly three spoilage steps. The step 1 shows the lactic and phosphoric acid generating from glycogen and ATP. The sensor detected an acid value with a potential increase in the first 10 hours. At the step 2, the potential started to drop after 12 hours indicating a change to alkaline. This is because the protein was decomposed to amino acid by enzyme. The pH level slightly increased and the potential dropped due to the amine from the amino acid. However, there were still some compositions such as $CO_2$, lactic acid and etc left in the muscle. The pH level may drop due to neutralization of the alkaline elements by residual acidic elements. In the step 3, a clear spoilage happened after 26 hours. The pH level increased and potential dropped because of the ammonia ($NH_4$). At the same time, the microbes started to grow and produced the compositions such as Indol, Scatol, and amino nitride etc, which generated a distinct odor.

The foregoing tests demonstrate that the flexible iridium oxide pH sensor detected the pH level changes due to the fish spoilage processes. The changes of potential detected by our sensor matched with the pH level variations corresponding to the spoilage phenomena reported in literatures.

Now referring back to FIG. 4, a multi-sensor array 400 is used to accurately monitor various parts of the meats/fishes in a package. In the test version, the multi-sensor array 500 is a 4×4 array with sixteen iridium oxide pH sensors on a flexible Kapton substrate. The size of the whole array 400 is around 3×3 $cm^2$. This sensor can detect the pH level distributions simultaneously across the same area. Each sensor is connected an individual RFID so each sensor information can be individually recorded. The Kapton film is deformable so all 16 sensors can touch their respective areas on the meat/fish firmly after wrapping and packaging.

Two Tilapia fillet samples were used to demonstrate the in situ monitoring of fish spoilage. One Tilapia filet was stored at 25° C. and the other filet sample was stored in a refrigerator at 5° C. A flexible sensor was placed under each filet samples with wires connected to the data acquisition card in the computer. A thin plastic wrap was used to wrap the filet tightly. The sensor potentials were recorded for 17 hours continuously at a sampling rate of 1 Hz.

Figure 30:
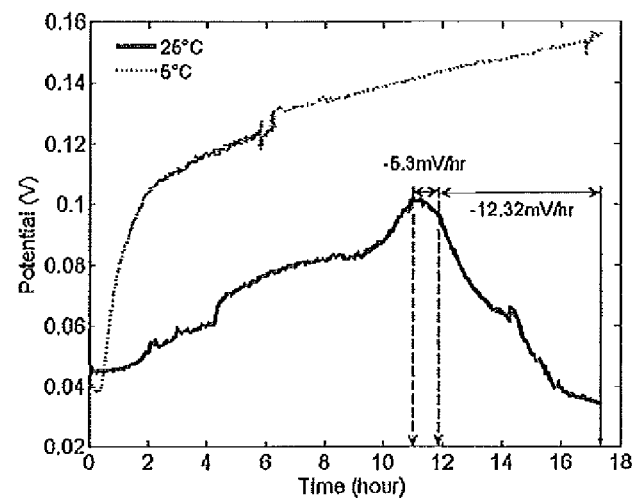
FIG. 30 is a graph showing the measured potential profiles in accordance with one aspect of the invention.

FIG. 30 shows the potential responses of the two filet samples. The sample stored at the room temperature did follow the mentioned spoilage steps. Within the first 11 hours, the potential increased from 45.8 mV to 101.7 mV which represented the pH level reduction due to the releasing of lactic acid. After 11 hours, the potential started to drop from 101.7 mV to 96.4 mV in one hour. The declined rate was −5.3 mV/hr. This is the second step in the spoilage process called autolysis during which the pH level slightly increases due to the releasing of amino groups from dead muscles. From the $12^{th}$ to $17^{th}$ hour, the potential detected by our sensor dropped significantly from 96.4 mV to 34.8 mV with a rate of −12.32 mV/hr. The pH level increases due to the growth of microbes and absorption of the amino and protein groups. The microbes further create chemicals such as indole and skatole which are alkaline making the pH level increased. On the contrary, the fish sample stored at 5° C. in a refrigerator had the potentials increase slowly in 17 hours. There is a clearly distinct difference between these two fish samples. The potential profile for the pH level in the fish meat without an appropriate storage temperature shows the signature feature of spoilage and the rotten smell from the fish starting at the $13^{th}$ hour verified that. This experimental result indicated that we can potentially recognize the signatures of spoilage by detecting the pH variations to monitor the freshness of fish.

The present invention can also be used to wirelessly monitor the pH changes in food with a flexible pH sensor embedded in a passive RFID circuit for batteryless wireless communication. The RFID transponder can harvest RF power which transmits from a reader and then sends the modulated data back to the reader. A wireless sensor tag of the present invention includes a flexible pH sensor based on miniature iridium oxide ($IrO_x$) and silver chloride (AgCl) sensing electrodes integrated on a deformable substrate, and batteryless wireless communication circuitry. The sensor tag and reader system is designed to achieve convenient, long-term, and on-demand wireless in situ monitoring of food quality, especially for large-quantity applications and continuous monitoring from place of production to retail stores. Low-cost $IrO_x$ sol-gel fabrication process was applied on polymeric substrates to form the flexible sensing films, and a sensitivity of −49.7 mV/pH was achieved. Inducting coupling provides electromagnetic energy from the reader to drive the transponder circuits that re-transmit the sensor-data modulated signals back to the reader. The electrochemical potential created by the $IrO_x$/AgCl sensing electrodes is converted to a modulated frequency and the system achieves a sensitivity of 633 Hz/pH.

The wireless pH sensing system was tested for in situ monitoring of the spoilage processes in fish meats continuously for 17 hours. The wireless pH sensing system consisted of both the flexible pH sensor connected to the printed circuit board of a tag and the reader. The feasibility of wireless monitoring pH values in fish meats that could be used to identify spoilage remotely was demonstrated as follows.

Two Tilapia fillet samples were used to demonstrate wireless in situ monitoring of fish spoilage. The filets were prepared and tested at 25° C. and 5° C. as discussed above. A flexible sensor was placed under each filet samples with wires connected to a tag. The tag was placed on the side of the filet and the filet sample was wrapped tightly in plastic wrap. Readers were placed at a distance of 10 cm from the filets with coil antennas in the same orientation.

Figure 31:
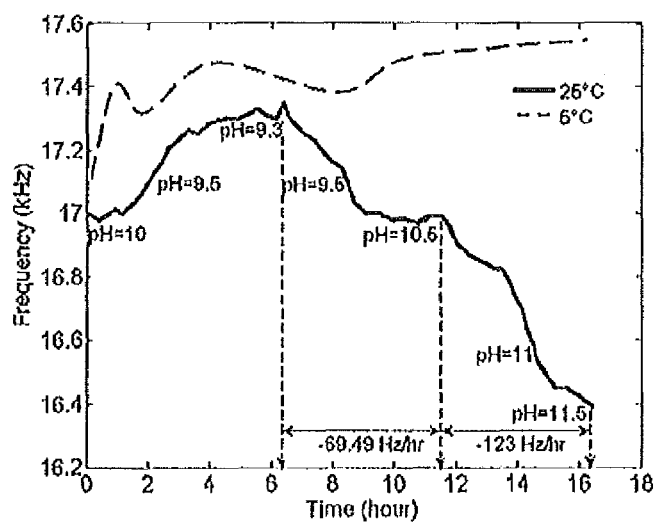
FIG. 31 is a graph showing modulated frequency profiles in accordance with another embodiment of the invention.

FIG. 31 shows the modulated frequency profiles during the 17-hour period for the two Tilapia samples at 25° C. and 5° C. Similar to the measured potentials shown in FIG. 30, there are two distinct frequency profiles showing the difference between the fish sample at the room temperature and the one in the refrigerator. The frequency profile for the fish sample stored at 25° C. for 17 hours showed the 3-step signature in a spoilage process. The frequency increased in the first 6.39 hours from 17 kHz to 17.35 kHz corresponding to the rigor mortis step. From the $6.39^{th}$ to $11.57^{th}$ hour, the frequency dropped from 17.35 to 16.99 kHz with a −69.49 Hz/hr decrease rate which represented the second step of spoilage. After the $11.57^{th}$ hour, the frequency dropped from 16.99 to 16.39 kHz with a rate of −123 Hz/hr indicating the increase of pH in the last step of spoilage. On the contrary, the frequency profile for the fish stored at 5° C. in the refrigerator showed a stable increase from 17.1 kHz to 17.5 kHz within the 17-hour period. With the sensitivity curve, the pH level variations during the spoilage processes were indentified in FIG. 31. The pH level of the spoiled fish started at around 10 and decreased to pH=9.35 in the first 6.39 hours. Then the pH level increased back to 10.5 in 5.18 hours, and 11.5 in another 5 hours. In this experiment, the spoilage steps of a fish filet could be identified remotely. The quality of fish filets under different storage conditions therefore can be monitored continuously and wirelessly.

The batteryless wireless pH sensor system provides a direct and convenient means to monitor produce/food quality to address food safety and waste issues. The $IrO_x$ pH sensing electrodes are fabricated on flexible substrates that can be deformed on food surfaces to detect pH values. Experimental results show a good correlation between pH and electrochemical potential. The sensor sensitivity, stability and reversibility of the flexible pH sensors were tested with good performance. The electrochemical sensor device architecture allows integration with a batteryless transducer which has a similar operating principle of a RFID. This enables the applications of a sensor-embedded RFID which not only can be used for large-scale product inventory but also real-time quality monitoring of individual products.

The flexible pH sensor was integrated with a batteryless wireless transducer made on a printed circuit board. For future applications, a RFID chip can be bonded directly on the flexible substrate where the flexible sensor and a planar coil antenna are fabricated in the same batch processes. The sensor system was tested in terms of sensitivity and stability as well as in titration showing good performance in transduction of pH levels in solution. Both the flexible pH sensor and the batteryless wireless pH sensor system were used in the monitoring of fish meats. The results of pH profiles and measured frequency profiles for the fishes stored at the room temperature matched with the major signature steps in spoilage processes. There were distinct differences between the frequency/pH profiles for the fishes stored properly in the refrigerator and those stored improperly at the room temperature. Comparing with the traditional methods to monitor food freshness such as using gas sensors to detect certain volatile from foods, sensors to detect specific enzymes in foods, or simply monitoring the storage temperature, the wireless pH sensors provide an attractive alternative to monitor food quality as the flexible pH sensor could directly detect the chemical reactions in foods and the batteryless wireless transducer system architecture allows integration of inventory capability and real-time on-demand or continuous sensing functionality.

Figure 32:
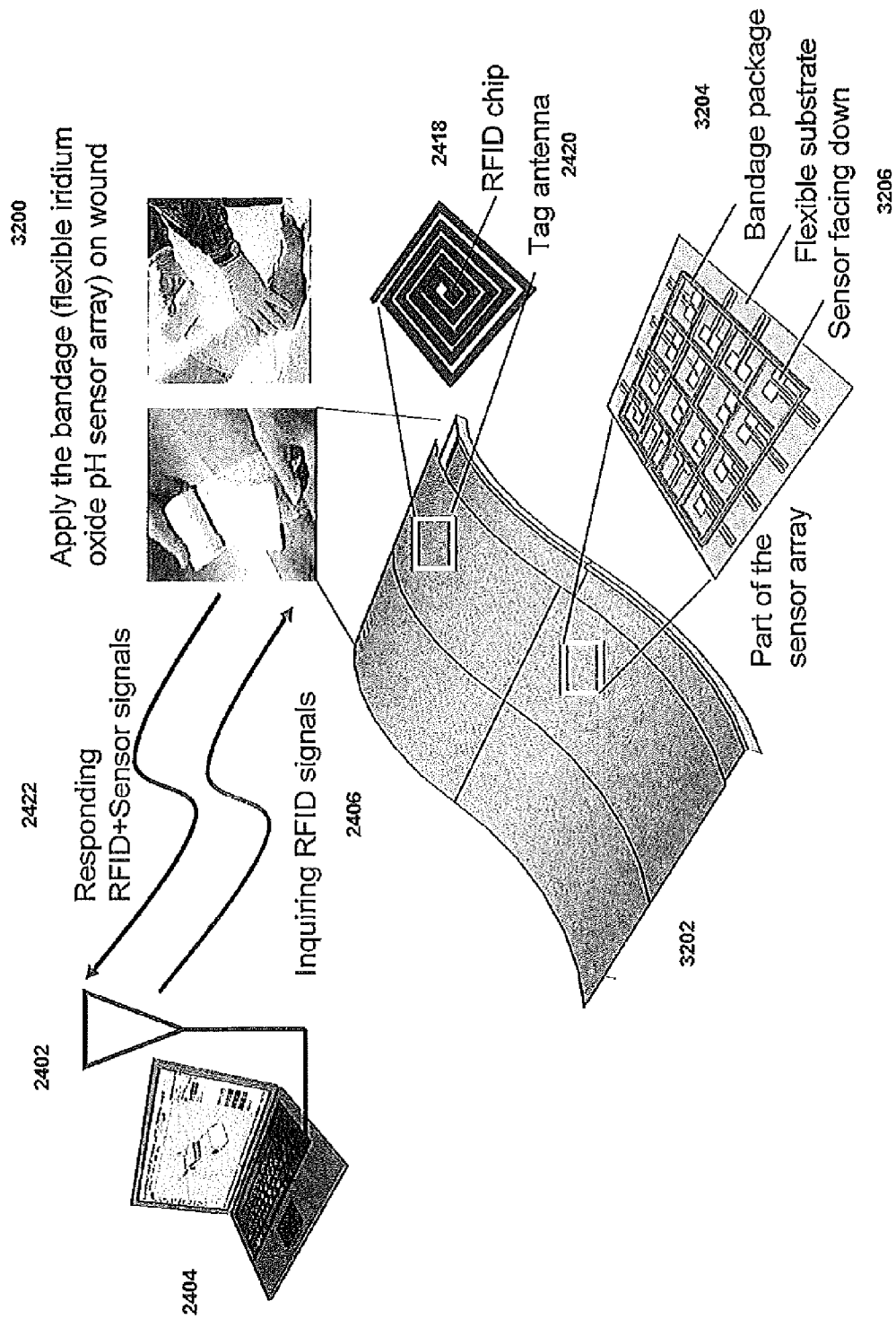
FIG. 32 is a diagram illustrating a wound condition monitoring system in accordance with another embodiment of the present invention.

Referring now to FIG. 32, a diagram illustrating a wound condition monitoring system 3200 in accordance with another embodiment of the present invention is shown. Wound healing is a sophisticated immune process which is represented by intercalating degradation, tissue re-assembly, and epidermal layer [53]. It is important to monitor the wound condition while the patient wears a bandage for two reasons: (1) the bandage should be changed according to the wound conditions, and (2) the different therapy agents need to be applied with respect to the wound conditions during various stages in wound healing.

For serious wound conditions, the bandage changes are done by doctors or nurses. In a hospital or trauma center, frequent changes of bandage add significant manual labors and therefore costs. Currently, the changes of bandages are done at fixed time schedules. This is not cost effective since sometimes the bandages may not need to be changed. Unnecessary changes of bandages may cause further damage to the wounds. It is also not result effective since some of the bandages need more frequent changes at certain stages of therapy, while others should not be changed in order to avoid tissue damages. However, the caretakers may not know when is the best time to change the bandages since most of the bandages are not transparent. The bandages need to be removed in order to examine the conditions of the wounds. With the fast growing of healthcare costs, frequent visits by the doctors or nurses to the patients' bedsides may not be preferable by the hospitals.

One of the significant applications is an example of wound care in a disaster site. Problems that start in the traumatic disaster complicate the entire wound care and recovery process. Enormous energy released by the injuring weapon or causes results in massive releases of signaling agents from the blasted tissues that are interpreted by the body as messages to "over-heal". The result is gross inflammation, unregulated and rapid growth of tissues in the injury site, and massive agglomeration of sear tissue. Such over-healing is detrimental to future recovery efforts as it tangles the wound into a random configuration and hides the structure of the original injury, both of which greatly complicate surgical reconstruction. Excessive bone deposits (heterotopic bone formation) and unregulated nerve regeneration (causing neuromas) will negatively impact numerous phases of future healing. The pain signals related to these growths result in long-term debilitation and additional nerve damage. Excessive scarring contracts tissues with incredible forces, grotesquely distorting the appearance of the tissues, affecting circulation and causing numerous other problems. Furthermore, Injuries tend to embed microscopic contaminants into the body of the wound, which result in high rates of infection. Active wound monitoring and infection management are crucial during this stage to ameliorate the likelihood and severity of infections.

In the recovery period, regeneration of massive hard and soft tissue deficit is the goal. An adaptive wound monitoring and management with tissue engineering will require a continuous and convenient way for wound condition monitoring to coordinate comprehensive reconstructive surgery.

For normal wound conditions, patients who wear bandages also need to know the wound conditions before replacement or seeking for further medical cares. This can be categorized into two general applications: therapy and protection. For therapy applications, wound conditions are monitored to reduce scar forming and promote stable tissue re-growth. For protection applications, the wounds are monitored to prevent infection.

Current solutions rely mainly on passive bandages for wound management without a monitoring mechanism. There is a strong need for a continuous, systematic yet flexible and reconfigurable wound monitoring that is lightweight, easy to implement and that provides ability to track patient's conditions.

pH value is an important indication to determine wound conditions with respect to its bacterial level. The pH distribution in the large wound area is useful information during the recovering and therapy procedures. A pH sensor array on flexible substrates in accordance with the present invention can be used to monitor pH level changes across an area of wound site. The metal oxide pH sensors allow continuous and long-term monitoring of pH, compared to the short lifetime disadvantage in enzyme-based or electrochemical sensing. The sensor is in an array configuration and on a flexible substrate allowing the sensor array to deform onto body parts to monitor multiple points in an area. The invented pH sensor produces a linear relationship between pH and potentials, which can be used in a batteryless wireless telemetry system. By detecting the responding shifted frequency of the modulated signals, the pH changes on the tissue can be monitored remotely.

As shown in FIG. 32, the flexible substrate conforms to the surface of wound. The sensor array 3206 contains multiple sensors 100 arranged in a particular spatial resolution. Each sensor 100 in the array 3206 detects the pH value in its respective spot. A RFID reader 2402+2404 transmits RF signal 3206 illuminating the wound area. The circuitry in the bandage 3202 harvests the radio-frequency energy 2406 to operate the sensor electrodes and a voltage-controlled oscillator. The oscillation frequency is controlled by the potential generated from the electrode. The modulated signal then is carried by the same resonant frequency carrier and retransmitted back 2422 to the reader 2402+2404. The reader 2402+2404 receives the responding signals 2422 and converts them to the baseband. The frequency shifts in the baseband signals indicate the pH values.

The reader antenna 2402 connected to a computer 2404 (or PDA and other wearable electronic devices on the patient's belt) sends out RFID inquiring signals 2406 to the patient. In the bandage 3202, it consists of an iridium oxide pH sensor array 3206 fabricated on a flexible substrate, a RFID chip 2418 and a tag antenna 2420. The sensor 100 touching the wound area senses the pH level and produces responding potentials. When the inquiring RFID signal 2406 sent by the reader 2402+2404 and received by the tag antenna 2420 has the inquiring ID matched with the ID in the bandage chip 2418, the chip 2418 harvests the received radio-frequency signal powers 2406 and uses the powers to operate the sensor and circuitry. The RFID chip 2418 then sends out the RFID and sensor data back to the reader 2402+2404 with the same carrier. The reader antenna 2402 connected to the computer 2404 receives the signals 2422, verifies the RFID 2418 and logs the sensor data into the computer 2404. Note that a visual indicator could be added to the exterior of the bandage 3202 to indicate the pH of the wound.

The normal pH level of human skin is between pH 4-7 [53] which depends on age, sex, and race of the person. The different location of skin also has different pH value. Harrison and Walker mentioned that the pH of human's dermis was 7.54±0.09 tested by glass pH electrode [54]. The physiological pH value is affected by amino acids, fatty acids, and others produced by the skin appendages [53].

In the beginning of an infection, the pH level of tissue may decrease because the bacteria share the nutrients and oxygen with the tissue cells. The phenomenon is called ischemic condition which may result the metabolism of tissue cells becoming anaerobic and therefore acidic [55].

In a chronic wound, there are different bacteria such as *staphylococcus aureus* and enzymes such as staphylococci may contaminate the wound area and delay the healing process. Some results in in-vitro experiment showed those microbes perform the overgrowth and active activity in higher pH level milieu [53]. In another study, the high-level pH environment slowed down the cell migration and DNA synthesis during the healing process [56].

In the literature [54], the animal and clinical studies have been done and shown an approximately linear response between the number of bacteria and the pH level. With an increase in bacteria counts, the pH level decreases. In the publication [53], the wound pH values were measured by an invasive glass electrode showing that the pH value dropped from 7.4 to 6.6 in the wound healing process. The wound condition was shown improved with the pH value decreased.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification, but only by the claims.

REFERENCES

[1] John G. Webster, "The measurement, instrumentation and sensors handbook," *CRC Press and IEEE Press*, pp. 71, Florida, 1999.

[2] Young-Jin Kim, Young-Chul Lee, Byung-Ki sohn, Jung-Hee Lee, and Chang-Soo Kim, "A novel pH microsensor with a buile-in reference electrode", *Journal of the Korean Physical Society*, Vol. 43, pp. 769-772, 2003.

[3] Yi Liu, Tianhoung Cui, "Ion-sensitive field-effect transistor based pH sensors using nano self-assembled polyelectrolyte/nanoparticle multilayer films," *Sensors and Actuators B*, Vol, 123, pp. 148-152, August, 2006.

[4] Jinghong Han, Dafu Cui, Yating Li, Hong Zhang, Yuzi Huang, Zipan Zheng, Yarning Zhu and Xiangrning Li, "A gastroesophageal tract pH sensor based on the H-ISFET and the monitoring system for 24 h," *Sensors and Actuators B*, Vol. 66, pp. 203-204, July, 2000.

[5] Kalman Pasztor, A. Sekiguchi, N. Shimo, N. Kitamura and H. Masuhara, "Iridium oxide-based microelectroehemical transistors for pH sensing," *Sensors and Actuators B*, Vol. 12, pp. 225-230, 1993.

[6] Otto S. Wolfbeis, "Fiber-optic chemical sensors and biosensors," *Anal. Chem.*, Vol. 76, pp. 3269-3284, 2004.

[7] Sheila A. Grant, Robert S. Glass, "A sol-gel based fiber optic sensor for local blood pH measurements," *Sensors and Actuators B*, Vol. 45, pp. 35-42, 1997.

[8] Saying Dong, Ming Luo, Gangding Peng, and Wenhua Cheng, "Broad range pH sensor based on sol-gel entrapped indicators on fiber optic," *Sensor and Actuators B: Chem.* Vol. 129, pp. 94-98, January, 2008.

[9] Zhe Jin, Yongxuan Su, and Yixiang Duan, "An improved optical pH sensor based on polyaniline," *Sensors and Actuators B*, Vol. 71, pp. 118-122, November, 2000.

[10] Afsaneh Safavi, Mozhgan, "Novel optical pH sensor for high and low pH values," *Sensors and Actuators B*, Vol. 90, pp. 143-150, April, 2003.

[11] E. Alvarado-Mendez, R. Rojas-Laguna, J. A. Andrade-Lucio, D. Hernandez-Cruz, R. A. Lessard, and J. G. Avina-Cervantes, "Design and characterization of pH sensor based on sol-gel silica layer on plastic optical fiber," *Sensors and Actuators B*, Vol. 106, pp. 518-522, May, 2005.

[12] Norman F. Sheppard, Jr., Matthew J. Lesho, Philip McNally, and A. Shaun Francomacaro, "Microfabricated conductimetric pH sensor," *Sensors and Actuators B*, Vol. 28, pp. 95-102, August, 1995.

[13] Gerald Gerlach, Margarita Guenther, Joerg Sorber, Gunnar Suchaneck, Karl-Friedrich Arndt, and Andreas Richter, "Chemical and pH sensors based on the swelling behavior of hydrogels," *Sensors and Actuators B*, Vol. 111-112, pp. 555-561, November, 2005.

[14] R. Bashir, J. Z. Hilt, O. Elibol, A. Gupta and N. A. Peppas, "Micromechanical cantilever as an ultrasensitive pH microsensor," *Applied Physics Letters*, Vol. 81, pp. 3091-3093, 2002.

[15] Agner Fog, Richard P. Buck, "Electronic semiconducting oxides as pH sensors," *Sensors and Actuators*, Vol. 6, pp. 137-146, 1984.

[16] T. Mikolajick, R. Kuhnhold, and H. Ryssel, "The pH-sensing properties of tantalum pentoxide films fabricated by metal organic low pressure chemical vapor deposition," *Sensors and Actuators B*, Vol. 44, pp. 262-267, 1997.

[17] Patrick J. Kinlen, John E. Heider, and David E. Hubbard, "A solid-state pH sensor based on a Nafion-coated iridium oxide indicator electrode and a polymer-based silver chloride reference electrode," *Sensors and Actuators B*, Vol. 22, pp. 13-25, October, 1994.

[18] H. Neil McMurray, Peter Douglas, and Cuncan Abbot, "Novel thick-film pH sensors based on ruthenium dioxide-glass composites," *Sensors and Actuators B*, Vol. 28, pp. 9-15, July, 1995.

[19] Wouter Olthuis, "Chemical and physical FET based sensors or variations on an equation," *Sensor and Actuator B*, Vol. 105, pp. 96-103, 2005.

[20] yl-Hung Liao and Jung-Chuan Chou, "Preparation and characteristics of ruthenium dioxide for pH array sensors with real-time measurement system," *Sensor and Actuators B: Chem.*, Vol. 128, pp. 603-612, January, 2007.

[21] Chu-Neng Tsai, Jung-Chuan Chou, Tai-Ping Sun, and Shen-Kan Hsiung, "Study on the sensing characteristics and hysteresis effect of the tin oxide pH electrode," *Sensors and Actuators B*, Vol. 18, pp. 877-882, July, 2005.

[22] Sheng Yao, Min Wang, and Marc Madou, "A pH electrode based on melt-oxidized iridium oxide," *Journal of the Elecvtrochemical Society*, Vol. 148, pp. 29-36, 2001.

[23] J. V. Dobson, P. R. Snodin and H. R. Thirsk, "EMF measurements of cells employing metal-metal oxide electrodes in aqueous chloride and sulphate electrolytes at temperatures between 25-250° C.," *Electrochimica Acta*, Vol. 21, pp, 527-533, 1976.

[24] T. Katsube, I. Lauks and J. N. Zemel, "pH-sensitive sputtered iridium oxide films," *Sensors and Actuators*, Vol. 2, pp. 399-410, 1981.

[25] M. F. Yuen, I. Lauks, and W. C. Dautremont-Smith, "pH dependent voltanmmetry of iridium oxide films," *Solid State Ionics*, Vol. 11, pp. 19-29, 1983.

[26] Kazusuke Yamanaka, "Anodically electrodeposited iridium oxide films (AEIROF) from alkaline solutions for electrochromic display devices," *Japanese Journal of Applied Physics*, Vol. 28, pp. 632-637, 1989.

[27] Michel A. Petit, Vincent Plichon, "Anodic electrodeposition of iridium oxide films," *Journal of Electroanalytical Chemistry*, Vol. 444, pp. 247-252, 1998.

[28] Sayed A. M. Marzouk, Stefan Ufer, Richard P. Buck, Timothy A. Johnson, Larry A. Dunlap, and Wayne E. Cascio, "Electrodeposited iridium oxide pH electrode for measurement of extracellular myocardial acidosis during acute ischemia," *Anal. Chem.*, Vol. 70, pp. 5054-5061, 1998.

[29] Igor A. Ges, Borislav L. Ivanov, David K. Schaffer, Eduardo A. Lima, Andreas A. Werdich, and Franz J. Baudenbacher, "Thin-film IrOx pH microelectrode for microfluidic-based Microsystems," *Biosensors and Bioelectronics*, Vol. 21, pp. 248-256, 2005.

[30] K. Nishio, Y. Watanabe, T. Tsuchiya, "Preparation and properties of electrochromic iridium oxide thin film by sol-gel process," *Thin Solid Films*, Vol. 350, pp. 96-100, 1999.

[31] Akiyoshi Osaka, Torn Takatsuna and Yoshinari Miura, "Iridium oxide films via sol-gel processing," *Non-Crystalline Solids*, pp. 313-319, 1994.

[32] Keishi Nishio and Toshio Tsuchiya, "Electrochromic thin films prepared by sol-gel process," *Solar Energy Materials & Solar Cells*, Vol. 68, pp. 279-293, 2001.

[33] C. Jefferey Brinker, George W. Scherer, *Sol-Gel Science: The physics and Chemistry of Sol-Gel Processing*, pp. 788-798, Academic Press, Boston, 1990.

[34] Sheila A. Grant, Kerry Bettencourt, Peter Krulevitch, Julie Hamilton and Robert Glass "In vitro and in vivo measurements of fiber optic and electrochemical sensors to monitor brain tissue pH," *Sensors and Actuators*, Vol 72, pp. 174-179, January, 2001.

[35] Sayed A. M. Marzouk, Stefan Ufer, Richard P. Buck, Timothy A, Johnson, Larry A. Dunlap, and Wayne E. Cascio, "Electrodeposited iridium oxide pH electrode for measurement of extracellular myocardial acidosis during acute ischemia," *Anal. Chem.*, Vol. 70, pp. 5054-5061, 1998.

[36] Danny 0' Hare, Kin H. Parker, and C. Peter Winlove, "Metal-metal oxide pH sensors for physiological application," *Medical Engineering and Physics*, Vol. 28, pp 982-988, 2006.

[37] Haley R. Clark, Timothy A. Barbari, "Modeling the response time of an in vivo glucose affinity sensor," *Biotechnol. Prog.*, Vol. 15, pp. 259-266, 1999.

[38] L. L. Visch, P. Bergveld, W. Lamprecht, and E. J.'s-Gravenmade, "pH measurement with an ion sensitive field effect transistor in the mouth of patients with xerostomia," *IEEE Transactions on biomedical engineering*, Vol. 38, pp. 353-356, 1991.

[39] Robert J. Gillies, Natrarajan Raghunand, Maria L. Garcia-Martin, and Robert A. Gatenby, "pH imaging—A review of pH measurement methods and applications in cancers," *IEEE Engineering in medicine and biology magazine*, pp. 58-64, 2004.

[40] Alan H. Auerbach, Babs R. Soller, Robert A, Peura, and Russell F. Stahl, "Hypothermia effects microsensor measurement of tissue pH," *IEEE*, pp. 830-831, 1994.

[41] Erika Kress-Rogers, "Solid-state pH sensors for food application," *Elsevier Trends Journals*, Vol. 2, pp. 320-324, 1990.

[42] Cl. Bohnke, H. Duroy, and J.-L. Fourquet, "pH sensors with lithium lanthanum titanate sensitive material: applications in food industry," *Sensors and Actuators B*, Vol. 89, pp. 240-247, 2003.

[43] Matthew F. Smiechowski, Vadim F. Lvovich, "Iridium oxide sensors for acidity and basicity detection in industrial lubricants," *Sensors and Actuators B*, Vol. 96, pp. 261-267, November, 2003.

[44] Erno Pungor, "The theory of ino-selective electrodes," *The Japan Society for Analytical Chemistry*, Vol. 14, pp. 249-256, 1998.

[45] A. W. J. Cranny, J. K. Atkinson, "Thick film silver-silver chloride reference electrodes," *Meas. Sci Technol*, pp. 1557-1565, 1998.

[46] M. Pourbaix, "Atlas of electrochemical equilibria in aqueous solutions," *National Association of Corrosion Engineers*, pp. 374-377, 1974.

[47] S, Ardizzone, A. Carugati, S. Trasatti, "Properties of thermally prepared iridium dioxide electrodes," *J. Electroanal. Cheml.*, Vol. 126, pp. 287-292, 1981.

[48] J. Hendrikese, W. Olthuis, P. Bergveld, "A method of reducing oxygen induced drift in iridium oxide pH sensor," *Sensor and Actuator*, Vol 53, pp. 97-103, November, 1998.

[49] W. Olthuis, M. A. M. Robben, P. Bergveld, M. Bos and, W. E. van der Linden, "pH sensor properties of electrochemically grown iridium oxide," *Sensor and Actuators B*, Vol. 2, pp. 247-256, 1990.

[50] H. Andreas, H. Elzanowska, I. Serebrennikova, and V. Birss, "Hydrous Ir oxide film properties at sol-gel derived Ir nanoparticles," *Journal of The Electrochemical Society*, Vol. 147, pp. 4598-4604, 2000,

[51] Fang Yue, Tan Swee Ngin, and Ge Hailin, "A novel paper pH sensor based on polypyrrole," *Sensor and Actuators B*, Vol. 32, pp. 33-39, April, 1996.

[52] Thermpon Ativanichayaphong, Shou Jiang Tang, Jianqun Wang, Wen-Ding Huang, Harry F. Tibbals, Stuart J. Spechler, J.-C. Chiao, "An Implantable, Wireless and Batteryless Impedance Sensor Capsule for Detecting Acidic and Non-Acidic Reflux," *Digestive Disease Week* 2008, San Diego, May 17-22, 2008.

[53] Lars Alexander Schneider, Andreas Korber, Stephan Grabbe, and Joachim Dissemond, "Influence of pH on wound-healing: a new perspective for wound-therapy?" *Arch Dermatol Res*, Vol, 298, pp. 413-420, 2007.

[54] Harrison D K, Walker W F, "Micro-electrode Measurement of Skin pH in Humans During Ischaemia, Hypoxia and Local Hypothermia", *Journal of Physiology*, Vol. 291, pp. 339-350, 1979.

[55] Susan Margaret Shorrock, "The exploration of tissue pH in wounds and its relationship to bacterial contamination," *Master Degree Thesis*, Worcester Polytechnic Institute, pp. 20-24, 2000.

[56] Lengheden A, and Jansson L, "pH effect on experimental wound healing of human fibroblasts in vitro," *Eur J Oral Sciences*, Vol. 103, pp. 148-155, 1995.

[57] G. Papeschi, S. Bordi, C. Beni, and L. Ventura, "Use of an iridium electrode for direct measurement of pI of proteins after isoelectric focusing in polyacrylamide gel," *Biochimica et Biophysica Acta*, Vol. 453, pp, 192-199, 1976.

[58] G. M. da Silva, S. G. Lemos, L. A. Picrifka, P. D. Marreto, A. V. Rosario, and E. C. Pereira, "Development of low-cost metal oxide pH electrodes based on the polymeric precursor method," *Analytica Chimica Acta*, Vol, 616, pp. 36-41, 2008.

[59] S. Chen and V. Thomas, "Optimization of inductive RFID technology," *IEEE International Symposium on Electronics and the Environment*, pp. 82-87, 2001.

[60] E. Haile and J. Lepkowski, "Oscillator Circuits for RTD Temperature Sensors," *Application note AN895, Microchip Technology Inc.,* 2004.

The invention claimed is:

1. A method for fabrication of one or more pH sensors comprising the steps of:
   depositing a chromium layer and a gold layer on a flexible polymer substrate to define a sensor electrode and a first electrical contact pad;
   depositing a sacrificial layer on the first electrical contact pad and the flexible polymer substrate;
   coating the sacrificial layer and the sensor electrode with an iridium oxide thin film;
   heating the sensor electrode to form an amorphous iridium oxide sensor electrode;
   removing the sacrificial layer;
   depositing a chromium layer, a platinum layer and a silver layer on the flexible polymer substrate to define a reference electrode and a second electrical pad; and
   electroplating the silver layer.

2. The method as recited in claim 1, wherein:
   the flexible polymer substrate comprises a Kapton polyimide flexible substrate; and
   the sacrificial layer comprises SU-8.

3. The method as recited in claim 1, further comprising the steps of applying a sacrificial layer of S1813 to the chromium, platinum and silver layers.

4. The method as recited in claim 1, wherein an electron-beam evaporator deposits the chromium layer, the gold layer, the chromium layer, the platinum layer and the silver layer.

5. The method as recited in claim 1, wherein:
   the sacrificial layer and the sensor electrode are coated with the iridium oxide thin film by a dipcoating process; and
   the heating step comprises at 150 degrees Celsius for at least 1 hour followed by a second heating step of 300 degrees Celsius for another 5 hours after the sacrificial layer is removed.

6. The method as recited in claim 5, wherein the second heating step is performing in an oven purged with inert gas starting at 25 degrees Celsius and increasing to 300 degrees Celsius in a period of 2 hours, and staying at 300 degrees Celsius for another 5 hours.

7. The method as recited in claim 1, wherein the step of depositing the sacrificial layer comprises the steps of:
   depositing the sacrificial layer using a spin cycle;
   heating the sacrificial layer at 65 degrees Celsius for 3 minutes and then 10 minutes at 95 degrees Celsius; and
   developing and drying the sacrificial layer.

* * * * *

UNITED STATES PATENT AND TRADEMARK OFFICE
CERTIFICATE OF CORRECTION

| | | |
|---|---|---|
| PATENT NO. | : 9,163,313 B2 | Page 1 of 1 |
| APPLICATION NO. | : 14/037848 | |
| DATED | : October 20, 2015 | |
| INVENTOR(S) | : Jung-Chih Chiao and Wen-Ding Huang | |

It is certified that error appears in the above-identified patent and that said Letters Patent is hereby corrected as shown below:

Title Page, item (72):

Delete: "Jung-Chi Chiao"

Replace with: Jung-Chih Chiao

Signed and Sealed this
Seventh Day of June, 2016

Michelle K. Lee
*Director of the United States Patent and Trademark Office*